(12) United States Patent
Hampp et al.

(10) Patent No.: US 11,564,744 B2
(45) Date of Patent: Jan. 31, 2023

(54) SYSTEMS AND METHODS FOR SURGICAL PLANNING USING SOFT TISSUE ATTACHMENT POINTS

(71) Applicant: MAKO Surgical Corp., Fort Lauderdale, FL (US)

(72) Inventors: Emily Hampp, Far Hills, NJ (US); Sally LiArno, Bergenfield, NJ (US); Gokee Yildirim, Weehawken, NJ (US); Mark Ellsworth Nadzadi, Batavia, OH (US); Gavin Clark, Perth (AU)

(73) Assignee: MAKO Surgical Corp., Fort Lauderdale, FL (US)

( * ) Notice: Subject to any disclaimer, the term of this patent is extended or adjusted under 35 U.S.C. 154(b) by 501 days.

(21) Appl. No.: 16/721,344

(22) Filed: Dec. 19, 2019

(65) Prior Publication Data

US 2020/0205898 A1 Jul. 2, 2020

Related U.S. Application Data

(60) Provisional application No. 62/785,427, filed on Dec. 27, 2018.

(51) Int. Cl.
*A61B 34/10* (2016.01)
*A61B 34/30* (2016.01)
*G06T 7/00* (2017.01)

(52) U.S. Cl.
CPC ............ *A61B 34/10* (2016.02); *A61B 34/30* (2016.02); *G06T 7/0012* (2013.01);
(Continued)

(58) Field of Classification Search
CPC ... A61B 34/10; A61B 34/30; A61B 2034/105; A61B 2034/107; A61B 2034/108;
(Continued)

(56) References Cited

U.S. PATENT DOCUMENTS 8,010,180 B2 8/2011 Quaid et al.
9,101,393 B2 8/2015 Jordan et al.
(Continued)

FOREIGN PATENT DOCUMENTS

CA 2689511 A1 12/2008
EP 1 571 581 A1 9/2005
(Continued)

OTHER PUBLICATIONS

Kang et al. "Femoral component alignment in unicompartmental knee arthroplasty leads to biomechanical change in contact stress and collateral ligament force in knee joint." Archives of orthopaedic and trauma surgery 138.4 (Jan. 2018): 563-572. (Year: 2018).*
(Continued)

*Primary Examiner* — Katrina R Fujita
(74) *Attorney, Agent, or Firm* — Foley & Lardner LLP

(57) ABSTRACT

A surgical system includes a robotic device, a surgical tool mounted on the robotic device, and a processing circuit. The processing circuit is configured to receive image data of an anatomy, generate a virtual bone model based on the image data, identify a soft tissue attachment point on the virtual bone model, plan placement of an implant based on the soft tissue attachment point, generate a control object based on the placement of the implant, and control the robotic device to confine the surgical tool within the control object.

17 Claims, 16 Drawing Sheets

(52) U.S. Cl.
CPC ... *A61B 2034/105* (2016.02); *A61B 2034/107* (2016.02); *A61B 2034/108* (2016.02); *G06T 2207/10081* (2013.01); *G06T 2207/30008* (2013.01)

(58) Field of Classification Search
CPC ......... G06T 7/0012; G06T 2207/10081; G06T 2207/30008
See application file for complete search history.

(56) References Cited

U.S. PATENT DOCUMENTS

| | | | |
|---|---|---|---|
| 9,358,117 | B2 | 6/2016 | Collazo et al. |
| 9,588,583 | B2 | 3/2017 | Lightcap et al. |
| 9,649,195 | B2 | 5/2017 | Bechtold et al. |
| 9,668,871 | B2 | 6/2017 | Irwin et al. |
| 9,724,109 | B2 | 8/2017 | Nadzadi et al. |
| 9,842,394 | B2 | 12/2017 | Buisseret et al. |
| 10,085,804 | B2 | 10/2018 | Nortman et al. |
| 10,194,919 | B2 | 2/2019 | Axelson et al. |
| 10,314,599 | B2 | 6/2019 | Hampp et al. |
| 2003/0153978 | A1 | 8/2003 | Whiteside |
| 2006/0142656 | A1 | 6/2006 | Malackowski et al. |
| 2007/0249967 | A1 | 10/2007 | Buly et al. |
| 2009/0209884 | A1 | 8/2009 | Van Vorhis et al. |
| 2010/0153081 | A1* | 6/2010 | Bellettre ................. G06T 17/20 715/764 |
| 2011/0092804 | A1 | 4/2011 | Schoenefeld et al. |
| 2013/0144392 | A1 | 6/2013 | Hughes |
| 2013/0211792 | A1* | 8/2013 | Kang .................... A61B 34/30 703/1 |
| 2013/0317344 | A1 | 11/2013 | Borus et al. |
| 2014/0031664 | A1 | 1/2014 | Kang et al. |
| 2014/0066937 | A1* | 3/2014 | Wiebe, III ......... A61B 17/1764 606/88 |
| 2014/0228860 | A1* | 8/2014 | Steines .................. A61B 34/30 606/130 |
| 2014/0244220 | A1* | 8/2014 | McKinnon ................ A61F 2/02 703/1 |
| 2016/0045268 | A1 | 2/2016 | Keppler et al. |
| 2016/0045317 | A1* | 2/2016 | Lang .................... A61F 2/30942 700/98 |
| 2017/0020609 | A1* | 1/2017 | Wentorf ................. A61B 6/487 |
| 2017/0086859 | A1* | 3/2017 | Couture ................. A61B 34/10 |
| 2017/0340389 | A1* | 11/2017 | Otto ..................... A61B 5/1077 |
| 2017/0360513 | A1 | 12/2017 | Amiot et al. |
| 2018/0036083 | A1 | 2/2018 | Ferko et al. |
| 2018/0256256 | A1* | 9/2018 | May ...................... A61F 2/461 |
| 2018/0353298 | A1 | 12/2018 | Mistry et al. |
| 2019/0133775 | A1 | 5/2019 | Westrich et al. |
| 2019/0183411 | A1 | 6/2019 | Yildirim et al. |

FOREIGN PATENT DOCUMENTS

| | | |
|---|---|---|
| EP | 2 962 666 A1 | 1/2016 |
| EP | 3 089 710 | 11/2016 |
| EP | 3 190 531 A1 | 7/2017 |
| EP | 1 871 267 B1 | 9/2018 |
| WO | WO-2010/151564 | 12/2010 |
| WO | WO-2013/101753 | 7/2013 |

OTHER PUBLICATIONS

International Search Report and Written Opinion for International Application No. PCT/US2019/067583, dated Apr. 21, 2020, 18 pages.

* cited by examiner

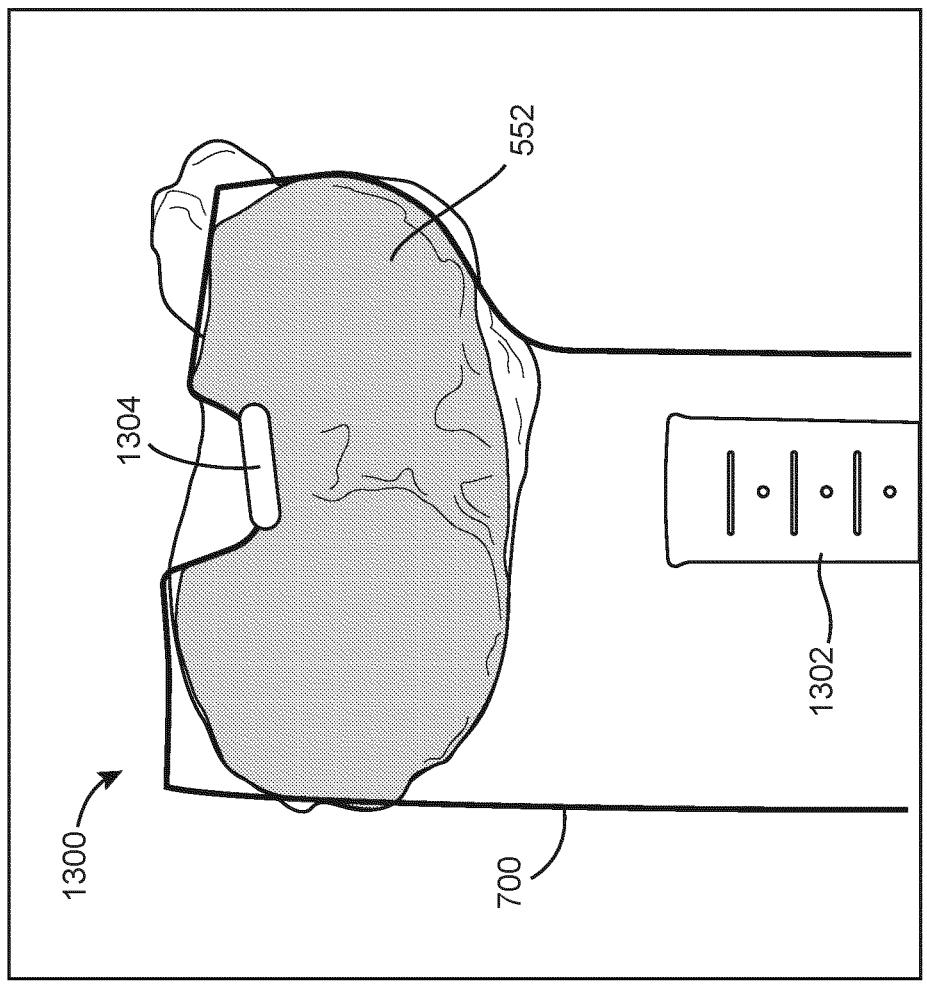

SYSTEMS AND METHODS FOR SURGICAL PLANNING USING SOFT TISSUE ATTACHMENT POINTS

CROSS-REFERENCE TO RELATED APPLICATION

This application claims the benefit of and priority to U.S. Provisional Patent Application No. 62/785,427, filed Dec. 27, 2018, the entire disclosure of which is incorporated by reference herein.

BACKGROUND

The present disclosure relates generally to the field of systems and methods for computer-assisted and robotically-assisted surgical procedures, and more particularly to the field of computer-assisted and robotically-assisted surgical systems for joint reconstruction procedures such as total knee arthroplasty (TKA). TKA is widely used to treat knee osteoarthritis and other damage to a patient's knee joint by replacing portions of the knee anatomy with prosthetic components. In a total knee arthroplasty procedure, a patient's femur and tibia are typically modified to be joined to a prosthesis using a series of planar cuts to prepare the surfaces of the bones. Prosthetic implants are then joined to the bone to form an artificial joint.

Computer-assisted surgical systems facilitate planning and execution of TKA procedures to assist in the modification of bones and implant alignment on the bones. However, conventional computer-assisted surgical systems often do not address issues involving soft tissue, for example ligaments such as the posterior cruciate ligament (PCL) and anterior cruciate ligament (ACL), or take soft tissue into account when creating a surgical plan. This may result in iatrogenic soft tissue damage, weakening of attachment points between bone and soft tissue, impingement of ligaments by implant components, and other complications.

SUMMARY

One implementation of the present disclosure is a surgical system. The surgical system includes a robotic device, a surgical tool mounted on the robotic device, and a processing circuit. The processing circuit is configured to receive image data of an anatomy, generate a virtual bone model based on the image data, identify a soft tissue attachment point on the virtual bone model, plan placement of an implant based on the soft tissue attachment point, generate a control object based on the placement of the implant, and control the robotic device to confine the surgical tool within the control object.

In some embodiments, the soft tissue attachment point corresponds to a site where a posterior cruciate ligament or an anterior cruciate ligament attaches to a femur or a tibia. In some embodiments, the processing circuit is configured to plan placement of the implant based on the soft tissue attachment point by aligning an axis of the implant with a medial edge of the soft tissue attachment point.

In some embodiments, the processing circuit is further configured to generate a graphical user interface. The graphical user interface includes a visualization of the virtual bone model, the implant, and the soft tissue attachment point. In some embodiments, the graphical user interface includes a visualization of the control object. In some embodiments, the processing circuit is configured to restrict the control object from containing the soft tissue attachment point.

Another implementation of the present disclosure is a method. The method includes receiving image data of an anatomy, generating a virtual bone model based on the image data, identifying a soft tissue attachment point on the virtual bone model, determining implant size and placement based on the soft tissue attachment point, generating a control object based on the implant size and placement, constraining or controlling a surgical tool mounted on a robotic device based on the control object.

In some embodiments, the image data includes computed tomography images, and wherein the method also includes segmenting the computed tomography images to identify one or more bones in the images. In some embodiments, the soft tissue attachment point corresponds to a site where a posterior cruciate ligament or an anterior cruciate ligament attaches to a femur or a tibia. The soft tissue attachment point may correspond to a site where a patellar ligament attaches to a tibia. In some embodiments, determining implant placement includes aligning an axis of the implant with a medial edge of the soft tissue attachment point.

In some embodiments, the method also includes generating a graphical user interface that visualizes the virtual bone model, the implant, and the soft tissue attachment point. The graphical user interface may further provide a visualization of the control object. In some embodiments, the method includes predicting a line of action of a ligament based on the soft tissue attachment point, augmenting the virtual bone model with a virtual implant model of the implant, determining whether the line of action of the ligament intersects the virtual implant model, and, in response to a determination that the line of action of the ligament intersects the virtual implant model, providing an alert to a user. The method may include restriction the control object from containing the soft tissue attachment point.

Another implementation of the present disclosure is non-transitory computer-readable media storing program instructions that, when executed by one or more processors, cause the one or more processors to perform operations. The operations include receiving image data of an anatomy, generating a virtual bone model based on the image data, identifying a soft tissue attachment point on the virtual bone model, determining implant size and placement based on the soft tissue attachment point, generating a control object based on the implant size and placement, and constraining or controlling a surgical tool mounted on a robotic device based on the control object.

In some embodiments, the operations include restricting the control object from containing the soft tissue attachment point. In some embodiments, the operations include predicting a line of action of a ligament based on the soft tissue attachment point, augmenting the virtual bone model with a virtual implant model of the implant, determining whether the line of action of the ligament intersects the virtual implant model, and, in response to a determination that the line of action of the ligament intersects the virtual implant model, providing an alert to a user. In some embodiments, determining implant placement includes aligning an axis of the implant with a medial edge of the soft tissue attachment point.

This summary is illustrative only and is not intended to be in any way limiting. Other aspects, inventive features, and advantages of the devices or processes described herein will become apparent in the detailed description set forth herein,

BRIEF DESCRIPTION OF THE FIGURES

FIG. 13 is a fifth illustration of a graphical user interface generated by the processing circuit of FIG. 2, according to an exemplary embodiment.

DETAILED DESCRIPTION

Figure 1:
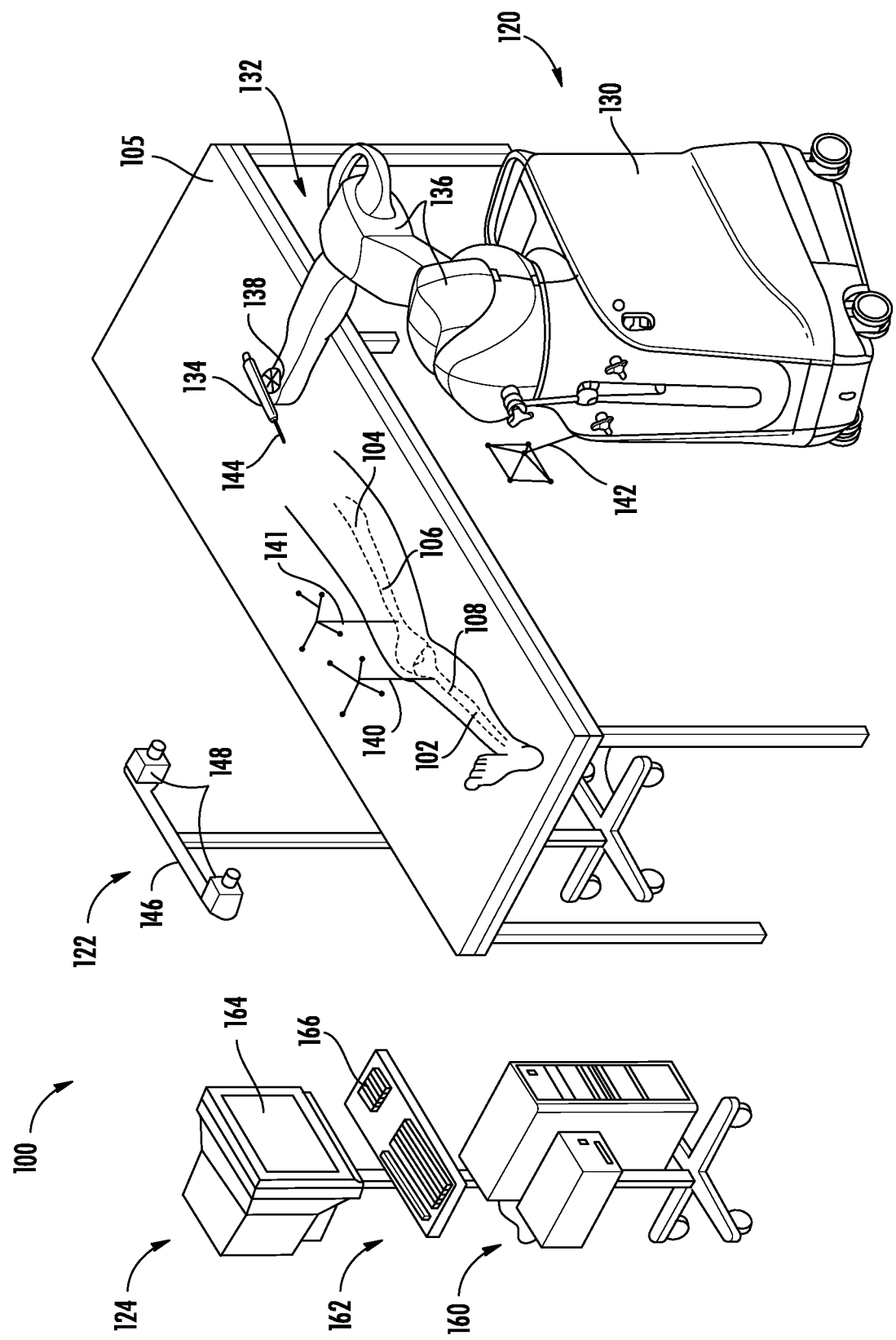
FIG. 1 is an illustration of a robotically-assisted surgical system, according to an exemplary embodiment.

Referring now to FIG. 1, a surgical system 100 for orthopedic surgery is shown, according to an exemplary embodiment. In general, the surgical system 100 is configured to facilitate the planning and execution of a surgical procedure. The surgical system 100 is configured to treat the anatomy of a patient, for example, as shown in FIG. 1, a leg 102 of a patient 104 sitting or lying on table 105. Leg 102 includes femur 106 and tibia 108, between which a prosthetic knee implant is to be implanted in a total knee arthroscopy procedure. The surgical system 100 may additionally or alternatively be configured to facilitate the planning and execution of partial knee arthroscopy procedures, total and/or partial hip arthroscopy procedures, other joint procedures, spinal procedures, and any other surgical procedure (e.g., neurosurgical, orthopedic, urological, gynecological, dental, ENT, oncological). To facilitate the procedure, surgical system 100 includes robotic device 120, tracking system 122, and computing system 124.

The robotic device 120 is configured to modify a patient's anatomy (e.g., femur 106 of patient 104) under the control of the computing system 124. One embodiment of the robotic device 120 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 120 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 120, in communication with the tracking system 122 and the computing system 124, may autonomously complete a series of cuts in a patients' bone or soft tissue without direct human intervention. According to various embodiments, the robotic device 120 may carry out various combinations of unrestricted surgeon-controlled actions, haptically-constrained actions, and/or automated or autonomous robotic actions.

The robotic device 120 includes a base 130, a robotic arm 132, and a surgical tool 134, and is communicably coupled to the computing system 124 and the tracking system 122. The base 130 provides a moveable foundation for the robotic arm 132, allowing the robotic arm 132 and the surgical tool 134 to be repositioned as needed relative to the patient 104 and the table 105. The base 130 may also contain power systems, computing elements, motors, and other electronic or mechanical system necessary for the functions of the robotic arm 132 and the surgical tool 134 described below.

The robotic arm 132 is configured to support the surgical tool 134 and provide feedback as instructed by the computing system 124. In some embodiments, the robotic arm 132 allows a user to manipulate the surgical tool 134 and provides force feedback to the user. In such an embodiment, the robotic arm 132 includes joints 136 and mount 138 that include motors, actuators, or other mechanisms configured to allow a user to freely translate and rotate the robotic arm 132 and surgical tool 134 through allowable poses while providing force feedback to constrain or prevent some movements of the robotic arm 132 and surgical tool 134 as instructed by computing system 124. As described in detail below, the robotic arm 132 thereby allows a surgeon to have full control over the surgical tool 134 within a control object while providing force feedback along a boundary of that object (e.g., a vibration, a force preventing or resisting penetration of the boundary). In some embodiments, the robotic arm 132 is configured to move the surgical tool 134 to a new pose automatically without direct user manipulation, as instructed by computing system 124, in order to position the robotic arm 132 as needed and/or complete certain surgical tasks, including, for example, cuts in a femur 106.

In alternative embodiments, the robotic device 120 is a handheld robotic device or other type of robot. In the handheld robotic device, a portion (e.g., end effector, surgical tool) of the handheld robotic device may be robotically controlled/actuated relative to a body of the handheld robotic device. A user may hold, support, and manipulate the handheld robotic device as desired while the robotically-actuated portion is controlled to facilitate the surgeon in executing a surgical procedure. For example, the handheld robotic device may be controllable to retract a surgical cutting tool to prevent the user from operating the surgical cutting tool in an unsafe area. It should be understood that the systems and methods described herein may be implemented with various robotic devices of various types, designs, configurations, etc.

In the embodiment shown, the surgical tool 134 is configured to cut, grind, drill, partially resect, reshape, and/or otherwise modify a bone. For example, surgical tool 134 may be configured to make a series of cuts in femur 106 to prepare the femur 106 and or tibia 108 to receive an implant. The surgical tool 134 may be any suitable tool, and may be one of multiple tools interchangeably connectable to robotic device 120. For example, as shown in FIG. 1 the surgical tool 134 is a spherical burr. The surgical tool 134 may also be a sagittal saw, for example with a blade aligned parallel with a tool axis or perpendicular to the tool axis. In other embodiments, the surgical tool 134 may be configured to execute one or more various other medical tasks (e.g., modifying soft tissue, implanting a prosthesis, generating an image, collecting data, providing retraction or tensioning).

Tracking system 122 is configured track the patient's anatomy (e.g., femur 106 and tibia 108) and the robotic device 120 (i.e., surgical tool 134 and/or robotic arm 132) to enable control of the surgical tool 134 coupled to the robotic arm 132, to determine a position and orientation of actions completed by the surgical tool 134 relative to the patient's anatomy, and allow a user to visualize the femur 106, the tibia 108, the surgical tool 134, and/or the robotic arm 132 on a display of the computing system 124. More particularly, the tracking system 122 determines a position and orientation (i.e., pose) of objects (e.g., surgical tool 134, femur 106) with respect to a coordinate frame of reference and tracks (i.e., continuously determines) the pose of the objects during a surgical procedure. According to various embodiments, the tracking system 122 may be any type of navigation system, including a non-mechanical tracking system (e.g., an optical tracking system), a mechanical tracking system (e.g., tracking based on measuring the relative angles of joints 136 of the robotic arm 132), or any combination of non-mechanical and mechanical tracking systems.

In the embodiment shown in FIG. 1, the tracking system 122 includes an optical tracking system. Accordingly, tracking system 122 includes a first fiducial tree 140 coupled to the tibia 108, a second fiducial tree 141 coupled to the femur 106, a third fiducial tree 142 coupled to the base 130, one or more fiducials 144 coupled to surgical tool 134, and a detection device 146 configured to detect the three-dimensional position of fiducials (i.e., markers on fiducial trees 140-142). As shown in FIG. 1, detection device 146 includes a pair of cameras 148 in a stereoscopic arrangement. The fiducial trees 140-142 include fiducials, which are markers configured to show up clearly to the cameras 148 and/or be easily detectable by an image processing system using data from the cameras 148, for example by being highly reflective of infrared radiation (e.g., emitted by an element of tracking system 122). The stereoscopic arrangement of the cameras 148 on detection device 146 allows the position of each fiducial to be determined in 3D-space through a triangulation approach. Each fiducial has a geometric relationship to a corresponding object, such that tracking of the fiducials allows for the tracking of the object (e.g., tracking the second fiducial tree 141 allows the tracking system 122 to track the femur 106), and the tracking system 122 may be configured to carry out a registration process to determine or verify this geometric relationship. Unique arrangements of the fiducials in the fiducial trees 140-142 (i.e., the fiducials in the first fiducial tree 140 are arranged in a different geometry than fiducials in the second fiducial tree 141) allows for distinguishing the fiducial trees, and therefore the objects being tracked, from one another.

Using the tracking system 122 of FIG. 1 or some other approach to surgical navigation and tracking, the surgical system 100 can determine the position of the surgical tool 134 relative to a patient's anatomical feature, for example femur 106, as the surgical tool 134 is used to make a cut in or otherwise modify the anatomical feature.

The computing system 124 is configured to create a surgical plan based on medical imaging or other data, receive data relating to the location of the surgical tool 134 and the patient's anatomy, and control the robotic device 120 in accordance with the surgical plan. In particular, in accordance with various embodiments described herein, the computing system 124 is configured to create a patient-specific surgical plan based on the location of and attachment points of soft tissue, and control the robotic device 120 using a control object that is patient-specific in accordance with the surgical plan. Accordingly, the computing system 124 is communicably coupled to the tracking system 122 and the robotic device 120 to facilitate electronic communication between the robotic device 120, the tracking system 122, and the computing system 124. Further, the computing system 124 may be connected to a network to receive information related to a patient's medical history or other patient profile information, medical imaging, surgical plans, surgical procedures, and to perform various functions related to performance of surgical procedures, for example by accessing an electronic health records system. Computing system 124 includes processing circuit 160 and input/output device 162. In some embodiments, a first computing device of computing system 124 (e.g., located in a surgeon's office, operated in a remote server) provides pre-operative features while a second computing device of computing system 124 (e.g., located in an operating room) controls the robotic device 120 and provides intraoperative features. According to various embodiments, the features and functions attributed herein to the computing system 124 may be implemented using any combination of or distribution between one or more devices, servers, cloud-based computing resources, etc.

The input/output device 162 is configured to receive user input and display output as needed for the functions and processes described herein. As shown in FIG. 1, input/output device 162 includes a display 164 and a keyboard 166. The display 164 is configured to display graphical user interfaces generated by the processing circuit 160 that include, for example, information about surgical plans, medical imaging, settings and other options for surgical system 100, status information relating to the tracking system 122 and the robotic device 120, and tracking visualizations based on data supplied by tracking system 122. The keyboard 166 is configured to receive user input to those graphical user interfaces to control one or more functions of the surgical system 100.

Figure 2:
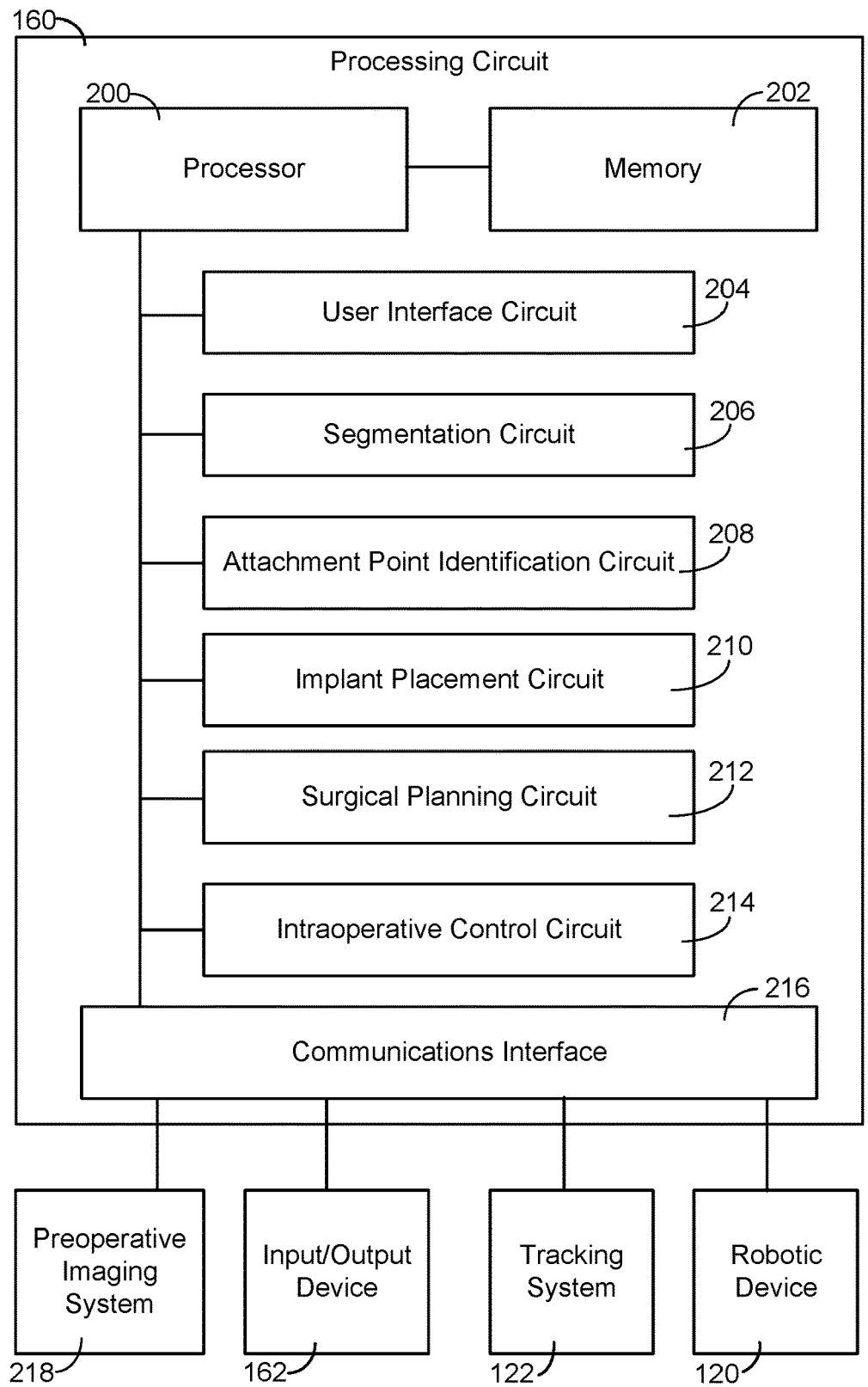
FIG. 2 is a block diagram of a processing circuit of the surgical system of FIG. 1, according to an exemplary embodiment.

The processing circuit 160 is configured to facilitate the creation of a preoperative surgical plan prior to the surgical procedure and to facilitate computer-assistance or robotic-assistance in executing the surgical plan. An exemplary embodiment of the processing circuit 160 is shown in FIG. 2 and described in detail below with reference thereto.

Still referring to FIG. 1, according to some embodiments the preoperative surgical plan is developed to be patient-specific utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 160 receives imaging data of the patient's anatomy on which the surgical procedure is to be performed (e.g., femur 106). The imaging data may be created using any suitable medical imaging technique to image the relevant anatomical feature, including computed tomography (CT), magnetic resonance imaging (MRI), and/or ultrasound. The imaging data is then segmented (i.e., the regions in the imaging corresponding to different anatomical features are distinguished) to obtain the virtual bone model. For example, MRI-based scan data of a knee is segmented to distinguish particular bones, ligaments, cartilage, and other tissue and processed to obtain a three-dimensional model of the imaged anatomy.

Alternatively, the virtual bone model may be obtained by selecting a three-dimensional model from a database or library of bone models. In one embodiment, the user may use input/output device 162 to select an appropriate model. In another embodiment, the processing circuit 160 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 160, input by a user via input/output device 162, or some combination of the two (e.g., the processing circuit 160 limits some features of user-created plans, generates a plan that a user can modify, etc.).

The preoperative surgical plan includes the desired cuts, holes, or other modifications to a patient's anatomy to be made using the surgical system 100. For example, for a total knee arthroscopy procedure as described herein, the preoperative plan includes the cuts necessary to form surfaces on the femur 106 and tibia 108 to facilitate implantation of a prosthesis. Accordingly, the processing circuit 160 may receive, access, and/or store a model of the prosthesis to facilitate the generation of surgical plans.

The processing circuit 160 is further configured to generate a control object for the robotic device 120 in accordance with the surgical plan. In some embodiments as described herein, the control objects are patient-specific based on the location of and attachment points of soft tissue. The control object may take various forms according to the various types of possible robotic devices (e.g., haptic, autonomous, etc.). For example, in some embodiments, the control object defines instructions for the robotic device 120 to control the robotic device 120 to move within the control object (i.e., to autonomously make one or more cuts of the surgical plan guided by feedback from the tracking system 122). In some embodiments, the control object includes a visualization of the surgical plan and the robotic device 120 on the display 164 to facilitate surgical navigation and help guide a surgeon to follow the surgical plan (e.g., without active control or force feedback of the robotic device 120). In embodiments where the robotic device 120 is a haptic device, the control object may be a haptic object as described in the following paragraphs.

In an embodiment where the robotic device 120 is a haptic device, the processing circuit 160 is further configured to generate one or more haptic objects based on the preoperative surgical plan, particularly in consideration of the location of and attachment points of soft tissue, to assist the surgeon during implementation of the surgical plan by enabling constraint of the surgical tool 134 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 134 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone (e.g., corresponding to the creation of surfaces intended to receive an implant).

In an embodiment where the robotic device 120 is a haptic device, the processing circuit 160 is further configured to generate a virtual tool representation of the surgical tool 134. The virtual tool includes one or more haptic interaction points (HIPs), which represent and are associated with locations on the physical surgical tool 134. In an embodiment in which the surgical tool 134 is a spherical burr (e.g., as shown in FIG. 1), an HIP may represent the center of the spherical burr. If the surgical tool 134 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 100 to constrain the surgical tool 134.

Prior to performance of a surgical procedure, the patient's anatomy (e.g., femur 106) may be registered to the virtual bone model of the patient's anatomy by any known registration technique. One possible registration technique is point-based registration, as described in U.S. Pat. No. 8,010,180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 134 to a virtual tool representation of the surgical tool 134, so that the surgical system 100 can determine and monitor the pose of the surgical tool 134 relative to the patient (i.e., to femur 106). Registration allows for accurate navigation, control, and/or force feedback during the surgical procedure.

The processing circuit 160 is configured to monitor the virtual positions of the virtual tool representation, the virtual bone model, and the control object (e.g., virtual haptic objects) corresponding to the real-world positions of the patient's bone (e.g., femur 106), the surgical tool 134, and one or more lines, planes, or three-dimensional spaces defined by forces created by robotic device 120. For example, if the patient's anatomy moves during the surgical procedure as tracked by the tracking system 122, the processing circuit 160 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated motions of robotic device 120 created during surgical planning that are linked to cuts, modifications, etc. to be made to that anatomy also move in correspondence with the patient's anatomy. In some embodiments, the surgical system 100 includes a clamp or brace to substantially immobilize the femur 106 to minimize the need to track and process motion of the femur 106.

For embodiments where the robotic device 120 is a haptic device, the surgical system 100 is configured to constrain the surgical tool 134 based on relationships between HIPs and haptic objects. That is, when the processing circuit 160 uses data supplied by tracking system 122 to detect that a user is manipulating the surgical tool 134 to bring a HIP in virtual contact with a haptic object, the processing circuit 160 generates a control signal to the robotic arm 132 to provide haptic feedback (e.g., a force, a vibration) to the user to communicate a constraint on the movement of the surgical tool 134. In general, the term "constrain," as used herein, is used to describe a tendency to restrict movement. However, the form of constraint imposed on surgical tool 134 depends on the form of the relevant haptic object. A haptic object may be formed in any desirable shape or configuration. As noted above, three exemplary embodiments include a line, plane, or three-dimensional volume. In one embodiment, the surgical tool 134 is constrained because a HIP of surgical tool 134 is restricted to movement along a linear haptic object. In another embodiment, the haptic object is a three-dimensional volume and the surgical tool 134 may be constrained by substantially preventing movement of the HIP outside of the volume enclosed by the walls of the three-dimensional haptic object. In another embodiment, the surgical tool 134 is constrained because a planar haptic object substantially prevents movement of the HIP outside of the plane and outside of the boundaries of the planar haptic object. For example, the processing circuit 160 can establish a planar haptic object corresponding to a planned planar distal cut of femur 106 in order to confine the surgical tool 134 substantially to the plane needed to carry out the planned distal cut.

For embodiments where the robotic device 120 is an autonomous device, the surgical system 100 is configured to autonomously move and operate the surgical tool 134 in accordance with the control object. For example, the control object may define areas relative to the femur 106 for which a cut should be made. In such a case, one or more motors, actuators, and/or other mechanisms of the robotic arm 132 and the surgical tool 134 are controllable to cause the surgical tool 134 to move and operate as necessary within the control object to make a planned cut, for example using tracking data from the tracking system 122 to allow for closed-loop control.

Referring now to FIG. 2, a detailed block diagram of the processing circuit 160 is shown, according to an exemplary embodiment. The processing circuit 160 includes a processor 200 and a memory 202. The processor 200 may be implemented as a general purpose processor, an application specific integrated circuit (ASIC), one or more field programmable gate arrays (FPGAs), a group of processing components, or other suitable electronic processing components. The memory 202 (e.g., memory, memory unit, storage device, etc.) includes one or more devices (e.g., RAM, ROM, Flash memory, hard disk storage, etc.) for storing data and/or computer code for completing or facilitating the various processes and functions described in the present application. The memory 202 may include volatile memory or non-volatile memory. The memory 202 may include database components, object code components, script components, or any other type of information structure for supporting the various activities and information structures described in the present application. According to an exemplary embodiment, the memory 202 is communicably connected to the processor 200 via the processing circuit 160 and includes computer code for executing (e.g., by the processing circuit 160 and/or processor 200) one or more processes described herein.

As shown in FIG. 2, the processing circuit 160 also includes a user interface circuit 204, a segmentation circuit 206, an attachment point identification circuit 208, an implant placement circuit 210, a surgical planning circuit 212, an intraoperative control circuit 214, and a communications interface 216. The various circuits 204-216 are communicably coupled to one another, to the processor 200 and memory 202, and to the communications interface 216. Although shown in as a unified device in FIG. 2, in some embodiments the processing circuit 160 and the elements thereof (i.e., the processor 200, memory 202, circuits 204-214, and communications interface 216) may be distributed among multiple computing devices, servers, robots, cloud resources, etc.

The communications interface 216 facilitates communication between the processing circuit 160 and the input/output device 162, the tracking system 122, and the robotic device 120 of FIG. 1. The communications interface 216 also facilitates communication between the processing circuit 160 and a preoperative imaging system 218 or other system (e.g., electronic health record, patient information database) configured to provide the processing circuit 160 with preoperative medical imaging of the patient's anatomy. The communications interface 216 may include cryptographic and encryption capabilities to establish secure communication sessions to prevent or substantially mitigate cybersecurity risks and to comply with patient health record privacy laws and regulations.

The user interface circuit 204 is configured to generate various graphical user interfaces to provide to one or more users via input/output device 162 and to receive, parse, and interpret user input to the input/output device 162. Example graphical user interfaces are shown in FIGS. 6-9 and described in detail with reference thereto. The user interface circuit 204 is communicably coupled to the various circuits 206-214 to receive information for display in graphical user interfaces from the circuits 206-214 and to provide user input to the circuits 206-214, as described in detail below.

The segmentation circuit 206 is configured to receive medical images from the preoperative imaging system 218, segment the medical images, and generate a three-dimensional virtual bone model based on the medical images. In various embodiments, medical images may be captured using one or more of various imaging techniques, including computed tomography (CT), magnetic resonance imaging (MM), ultrasound, etc. In the embodiments described herein, the segmentation circuit 206 primarily receives and utilizes CT images, and the following description references CT images/imaging. However, it should be understood that in various other embodiments, the processing circuit 160 may utilize various other types of medical images in addition to or in alternative to CT images, for example magnetic resonance imaging (MRI), ultrasound, and/or x-ray, including three-dimensional reconstruction/modeling from two-dimensional x-ray/fluoroscopic images.

The CT images received by the segmentation circuit 206 capture a plurality of views of the femur 106 and/or tibia 108 of the patient. The plurality of views may be a series of slices, i.e., cross-sectional views at each of a plurality of positions along the patient's leg. Each CT image may therefore show a two-dimensional slice of the patient's leg at a given position. The positions and order of the CT images may be known.

The segmentation circuit 206 is configured to segment the CT images to distinguish bone (e.g., the femur 106 and tibia 108) from surrounding tissue, fluid, etc. shown in the CT images. For example, the segmentation circuit 206 may determine a boundary of the bone shown in each CT image. In some embodiments, the segmentation circuit 206 automatically determines the boundary using automated image processing techniques (auto-segmentation). In other embodiments, the segmentation circuit 206 provides the CT images to the user interface circuit 204 for inclusion in a graphical user interface that prompts a user to input an indication of the boundary for each image. User input may be received that fully segments all images, or some combination of user input and auto-segmentation may be used. For example, a user may be prompted to check the accuracy of auto-segmentation and make adjustments as needed.

The segmentation circuit 206 is further configured to generate a virtual bone model (i.e., a three-dimensional model) based on the segmented CT images. In the embodiments shown, the segmentation circuit 206 generates a virtual bone model of the femur 106 and the tibia 108. The segmentation circuit 206 may use the bone boundaries in each CT image slice defined during segmentation, stack the image slices to organize the boundaries in order and separated at known distances, and generate a surface that conforms to the boundaries. The segmentation circuit 206 may thereby generate a virtual bone model defined as a three-dimensional surface, a collection of voxels, or some other representation in a given coordinate system.

The attachment point identification circuit 208 receives the virtual bone model from the segmentation circuit 206 and identifies one or more soft tissue attachment points on the virtual bone model. A soft tissue attachment point is a representation in the coordinate system of the virtual bone model of a site on a bone where soft tissue attaches to the bone, for example a point or region where a ligament attaches to a bone. According to various embodiments and for various soft tissues and/or procedures, a soft tissue attachment point may be defined as a point, a line, a surface, a voxel or collection of voxels, or some other representation.

In the embodiment shown herein, the attachment point identification circuit 208 identifies a posterior cruciate ligament (PCL) attachment point that corresponds to the site where the patient's PCL attaches to the patient's tibia 108.

In some embodiments, the attachment point identification circuit 208 also identifies an anterior cruciate ligament (ACL) attachment point that corresponds to a site where the patient's ACL attaches to the patient's tibia 108. The attachment point identification circuit 208 may also identify ligament attachment points corresponding to sites where the ACL and PCL attach to the femur 106. Various other soft tissue attachment points may also be identified.

In some embodiments, the attachment point identification circuit 208 identifies soft tissue attachment points automatically. For example, the attachment point identification circuit 208 may determine extrema, inflection points, or other identifiable features on the surface of the virtual bone model. As another example, the attachment point identification circuit 208 operates a neural network trained via machine learning to identify soft tissue attachment points.

In some embodiments, the attachment point identification circuit 208 identifies soft tissue attachment points by instructing the user interface circuit 204 to generate a graphical user interface that prompts a user to select a soft tissue attachment point on the virtual bone model. The user interface circuit 204 may generate a graphical user interface that visualizes the virtual bone model and provides a tool for selecting a point or points on the virtual bone model using the input/output device 162. The attachment point identification circuit 208 may receive the user input and define one or more soft tissue attachment points based on the user input.

Figure 5:
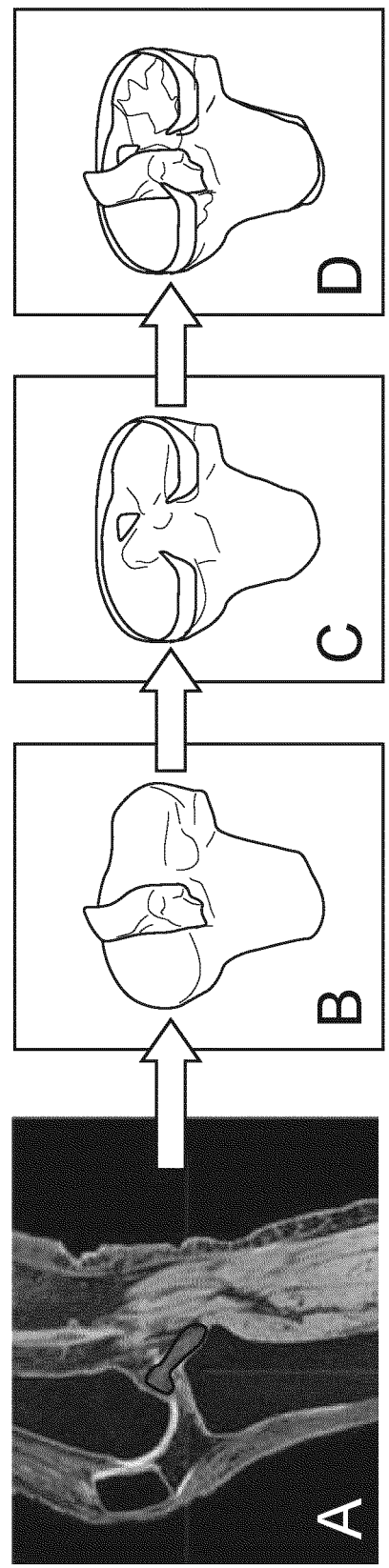
FIG. 5 is an illustration of using imaging of the bone to plan placement of an implant to avoid impingement in a knee arthroscopy procedure, according to an exemplary embodiment.
Figure 6:
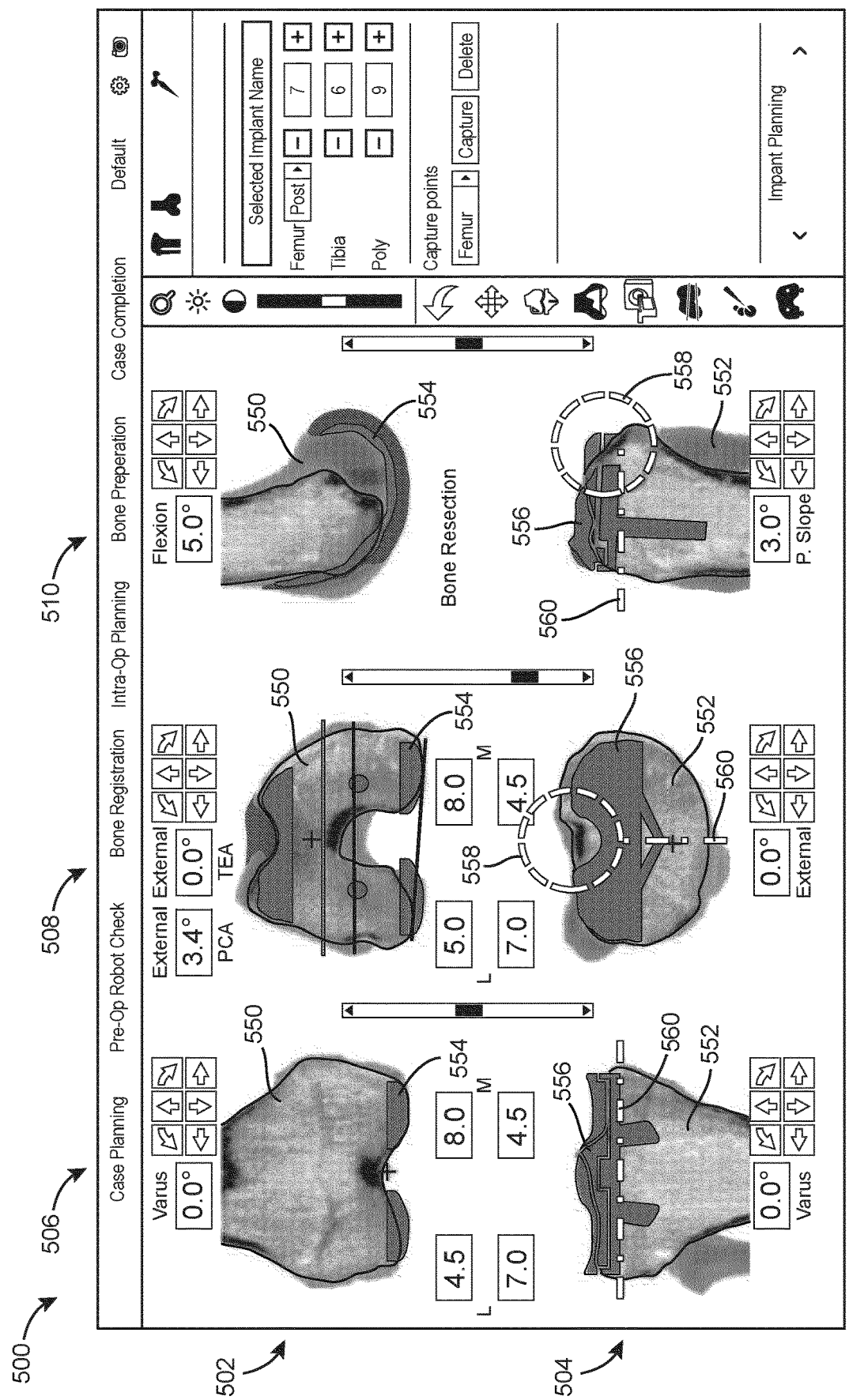
FIG. 6 is a first illustration of a graphical user interface generated by the processing circuit of FIG. 2, according to an exemplary embodiment.
Figure 7:
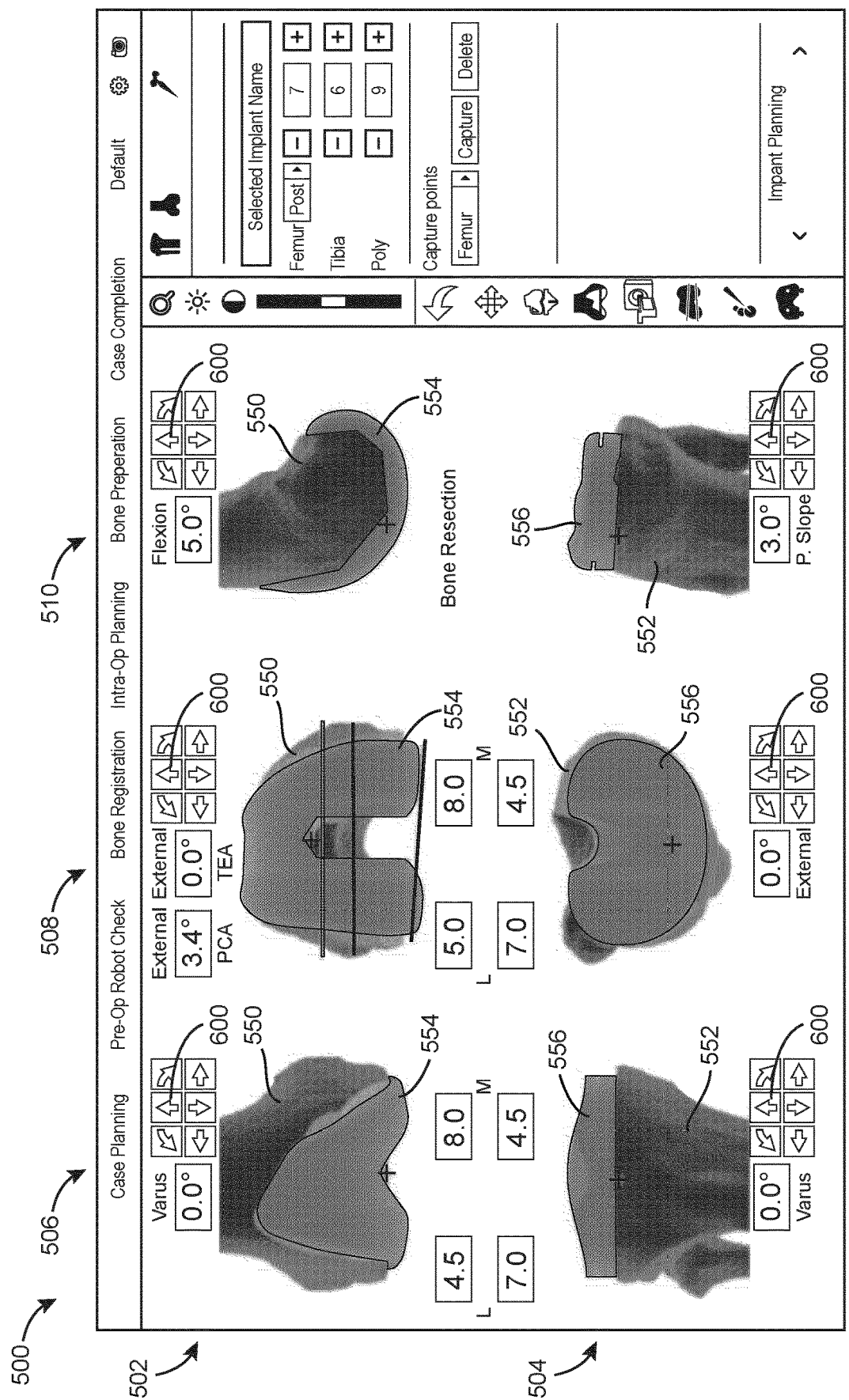
FIG. 7 is a second illustration of a graphical user interface generated by the processing circuit of FIG. 2, according to an exemplary embodiment.

The implant placement circuit 210 is configured to determine the size and placement of surgical implants based on the virtual bone model and the soft tissue attachment points. In some embodiments, the implant placement circuit 210 is configured to determine the placement of a tibial implant and a femoral implant for a total knee arthroscopy procedure based on the PCL attachment point on the tibia 108. In such embodiments, the implant placement circuit 210 overlays a virtual tibial implant on the virtual bone model of the tibia 108 and a virtual femoral implant on the virtual bone model of the femur 106. The implant placement circuit 210 positions the virtual tibial implant on the virtual bone model based on the PCL attachment point (e.g., to avoid interference with the PCL attachment point, to optimize rotation and coverage based on the PCL attachment point). FIG. 5 shows the use of imaging to identify the PCL attachment point on the bone model (frames A and B) and positioning a model of the implant on the bone model (frame C), and using the imaging to visually depict the relationship between the planned placement of the implant relative to the PCL (frame D) to determine whether impingement with the ligament might occur. A graphical user interface illustrating this alignment is shown in FIGS. 6-7.

In some embodiments, the implant placement circuit 210 is configured to predict the ACL and PCL line of action based on the PCL attachment points on the femur 106 and tibia 108 and the ACL attachment points on the PCL and ACL. That is, the implant placement circuit 210 is configured to generate a virtual ACL model and a virtual PCL model that predict the locations of the ACL and PCL between the tibia 108 and the femur 106. The implant placement circuit 210 may then place the virtual tibial implant and the virtual femoral implant to avoid impingement (i.e., obstruction, pinching, restriction, etc.) of the virtual ACL model and the virtual PCL model by the virtual tibial implant and the virtual femoral implant through a full range of motion of the knee. The implant placement circuit 210 may thereby facilitate the prevention of impingement of the ACL or PCL by implant components.

In some embodiments, the user interface circuit 204 generates a graphical user interface showing the placement of the virtual implants overlaid on the virtual bone models, for example as shown in FIGS. 6-9 and described in detail with reference thereto. The graphical user interface may allow a user to adjust the placement of the virtual implants. In such an embodiment, the implant placement circuit 210 may restrict the placement options available to the user to prevent the user from placing the virtual implants to interfere with an attachment point or to impinge the ACL or PCL. In other embodiments, the implant placement circuit 210 may generate an alert or warning (e.g., text message, audible alert) provided to input/output device 162 to inform the user of the interference or impingement while allowing the user to select such a placement.

The surgical planning circuit 212 receives the virtual bone model with virtual implants positioned thereon from the implant placement circuit 210. The surgical planning circuit 212 is configured to plan the cuts to the femur 106 and tibia 108 needed to prepare the femur 106 and the tibia 108 to receive the implants in the positions determined by the implant placement circuit 210. That is, the surgical planning circuit 212 determines how the femur 106 and the tibia 108 need to be modified such that femoral and tibial implants can be placed on the femur 106 and tibia 108 in the same positions as the virtual femoral and tibial implants are positioned on the virtual bone models by the implant placement circuit 210. The surgical planning circuit 212 may determine a surgical plan that includes a series of planned planar cuts to be made to the femur 106 and the tibia 108.

The surgical planning circuit 212 may be configured to adjust the planned cuts based on one or more soft tissue attachment points. For example, the surgical planning circuit 212 may be configured to ensure that the planned cuts do not intersect a soft tissue attachment point, weaken a soft tissue attachment point, intersect soft tissue attached to a soft tissue attachment point, or pose a risk of harm to soft tissue in some other way. If such a cut is required to place an implant in a position determined by the implant placement circuit 210, the surgical planning circuit 212 may send an error or warning message to the implant placement circuit 210 requesting that the implant placement circuit 210 revise the implant placement.

Based on the planned cuts, the surgical planning circuit 212 generates control objects (e.g., virtual haptic objects) for each of the planned cuts, which are based on the one or more soft tissue attachment points. Accordingly, the surgical planning circuit 212 uses the soft tissue attachment points to generate patient-specific control objects. Namely, the surgical planning circuit 212 may define one or more of the control objects to constrain the surgical tool from impacting one or more soft tissue attachment points. For example, a control object may correspond to a planar cut to be made to a distal surface of the tibia 108. The surgical planning circuit 212 may shape the control object such that the control object does not intersect the tibial PCL attachment point. FIGS. 8-9 show an illustration of such a control object, as described in detail below with reference thereto.

The intraoperative control circuit 214 is configured to facilitate implementation of the surgical plan generated by the surgical planning circuit 212. The intraoperative control circuit 214 is communicable with the tracking system 122 and robotic device 120 to perform registration, navigation, and tracking, for example as described above with reference to FIG. 1. The intraoperative control circuit 214 may register and track one or more soft tissue attachment points. The intraoperative control circuit 214 is also configured to control the robotic device 120 based on the control objects generated by the surgical planning circuit 212. In embodiments where the robotic device 120 is a haptic device, the intraoperative control circuit 214 controls the robotic device 120 to confine the surgical tool 134 to the control objects, for example as described above with reference to FIG. 1. In embodiments where the robotic device 120 is an autonomous or automated robotic device, the intraoperative control circuit 214 controls the robotic device 120 to move the surgical tool 134 within the control object to execute a cut or cuts, for example as described above with reference to FIG. 1. The intraoperative control circuit 214 may thereby protect one or more soft tissue attachment points during the surgical procedure by controlling the robotic device 120 in accordance with the control objects generated by surgical planning circuit 212.

Figure 3:
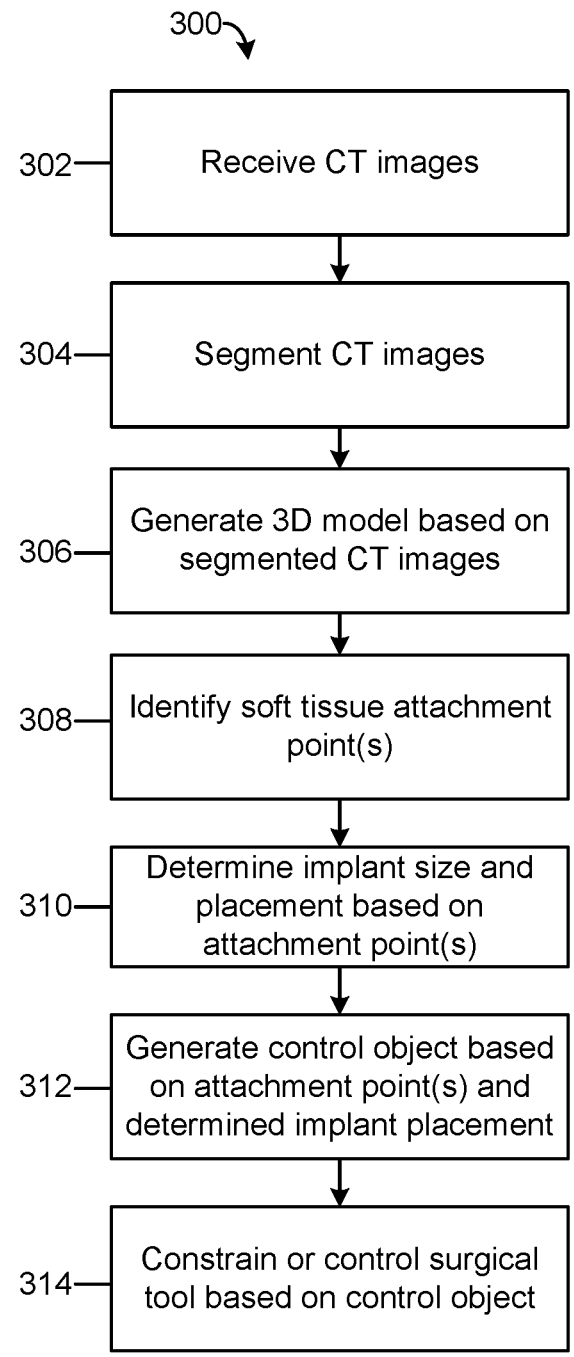
FIG. 3 is a flowchart of a process for facilitating a joint arthroscopy procedure, according to an exemplary embodiment.

Referring now to FIG. 3, a flowchart of a process 300 for facilitating a joint arthroscopy procedure using the location of one or more soft tissue attachment points is shown, according to an exemplary embodiment. Process 300 can be executed by the surgical system 100 of FIG. 1 and the processing circuit 160 of FIG. 2, and reference is made thereto in the following description. As described below, process 300 facilitates a total knee arthroscopy procedure. However, it should be understood that process 300 may be executed with various other systems and may be applicable to various other procedures, including partial knee arthroscopy, bicruciate retaining total knee arthroplasty, partial hip arthroscopy, and total hip arthroscopy, revision knee and hip procedures, among other procedures.

At step 302, the processing circuit 160 receives computed tomography (CT) images of the anatomy of interest, for example the tibia 108 and femur 106 of the leg 102 of the patient 104. The CT images may be captured by a preoperative imaging system 218 (e.g., a CT scanner) communicable with the processing circuit 160. The CT images may include a collection of two-dimensional images showing cross-sectional slices of the leg 102 at various positions along the leg 102.

At step 304, the CT images are segmented to distinguish the various tissues and structures shown in the images. For example, the region corresponding to the tibia 108 or femur 106 in each CT image may be determined. A boundary line that outlines the tibia 108 or femur 106 in each CT image may be defined and stored. In some embodiments, the processing circuit 160 automatically segments the CT images to distinguish regions corresponding to the tibia 108 or femur 106 from the rest of the image (i.e., parts of the image showing soft tissue or other anatomical structures). In other embodiments, the processing circuit 160 generates a graphical user interface that allows a user to manually input an indication of the boundary of the tibia 108 or femur 106 in each CT image. In still other embodiments, some combination of auto-segmentation and user input is used to increase the efficiency and accuracy of the segmentation process. The processing circuit 160 thereby acquires segmented CT images that indicate the shape/boundary of the tibia 108 and/or femur 106 at various layers along the tibia 108.

At step 306, the processing circuit 160 generates a virtual bone model of tibia 108 and/or femur 106 based on the segmented CT images. That is, the boundary of the tibia 108 and/or femur 106 defined in each segmented CT image is stacked, with the separation between each CT image known. The stack of images may then be processed to generate a three-dimensional virtual bone model representing the tibia 108 and/or femur 106 (e.g., a virtual tibia model and a virtual femur model).

At step 308, one or more soft tissue attachment points are identified on the virtual bone model. That is, one or more sites where soft tissue attaches to the tibia 108 or femur 106 are determined from the virtual bone model and/or the CT images. The coordinates of the sites in the coordinate system of the virtual bone model are determined and defined as soft tissue attachment points. For example, the PCL attachment point corresponding to the site where the PCL attaches to the tibia 108 may be identified and defined in this manner. In some embodiments, the processing circuit 160 generates a graphical user interface that allows the user to indicate or adjust the position of one or more soft tissue attachment points. An example of such a graphical user interface is shown in FIGS. 6-7 and described in detail with reference thereto. In some embodiments, the processing circuit 160 is configured to automatically identify one or more soft tissue attachment points.

In some embodiments, soft tissue attachment points are identified using bone density information visible in the CT images. For example, a site on a bone that attaches to soft tissue may have a higher density than other regions of the bone. These high-density areas may be distinguishable from a CT image, for example appearing more opaque or brighter in the CT image. The processing circuit 160 may use an image recognition technique or auto-segmentation approach to identify one or more areas in the CT images associated with high bone density and associate those areas with soft tissue attachment points. The processing circuit 160 may thereby automatically identify soft tissue attachment points based on bone density information captured by CT imaging.

At step 310, implant size and placement are determined based on the identified soft tissue attachment points. For example, the processing circuit 160 may generate a virtual implant model of a tibial implant and a femoral implant. The processing circuit 160 may then overlay the virtual implant model on the virtual bone model to assess sizing, positioning, orientation, alignment, etc. An example of a graphical user interface showing a virtual implant model overlaid on the virtual bone model is shown in FIGS. 6-7 and described in detail with reference thereto.

The processing circuit 160 may ensure that the implant model does not interfere with the one or more soft tissue attachment points by covering the attachment point, requiring removal or weakening of the attachment points, or causing impingement of a tendon by the implant. As one example, the processing circuit 160 may determine the size, position, and/or rotation of a tibial component of a knee implant based on the PCL attachment point on the tibia 108.

In some embodiments, the processing circuit 160 determines a rotation or orientation of the tibial component based attachment points corresponding to the PCL and the patellar ligament. More particularly, a line connecting the PCL attachment point and the patellar ligament attachment point may be used to set tibial component rotation. In some embodiments, one or more soft tissue attachment points are used as landmarks around which rotation may be defined or manipulated.

At step 312, the processing circuit 160 generates a patient-specific control object based on the implant size and placement determined at step 310 and based on one or more soft tissue attachment points. The control objects are configured to facilitate cuts or other modifications to the femur 106 and tibia 108 by the surgical tool 134 to prepare the femur 106 and tibia 108 to receive the femoral and tibial implants in the positions determined at step 310. The control object may be shaped and position to avoid intersection with or other interference with the soft tissue attachment points.

At step 314, the surgical tool 134 is control and/or constrained based on the control object. In embodiments where the robotic device 120 is an autonomous robotic system, the surgical tool 134 controlled to move autonomously through one or more control objects to modify the femur 106 and/or the tibia 108. Because the control object is shaped to avoid one or more soft tissue attachment points on the virtual bone model, the robotic device is controlled such that it does not contact the corresponding attachment sites on the real femur 106 or tibia 108 or the ligament or other tissue attached to said attachment sites. In embodiments where the robotic device 120 is a haptic device, the processing circuit 160 controls the robotic device 120 to constrain the surgical tool 134 within the control object. The surgical tool 134 is thereby constrained from contacting one or more attachment sites the ligament or other tissue attached to said attachment sites. A series of surgical cuts may thereby be carried out while protecting ligaments or other soft tissue from iatrogenic damage and limiting the risks of complications associated with weakened attachment points.

Figure 4:
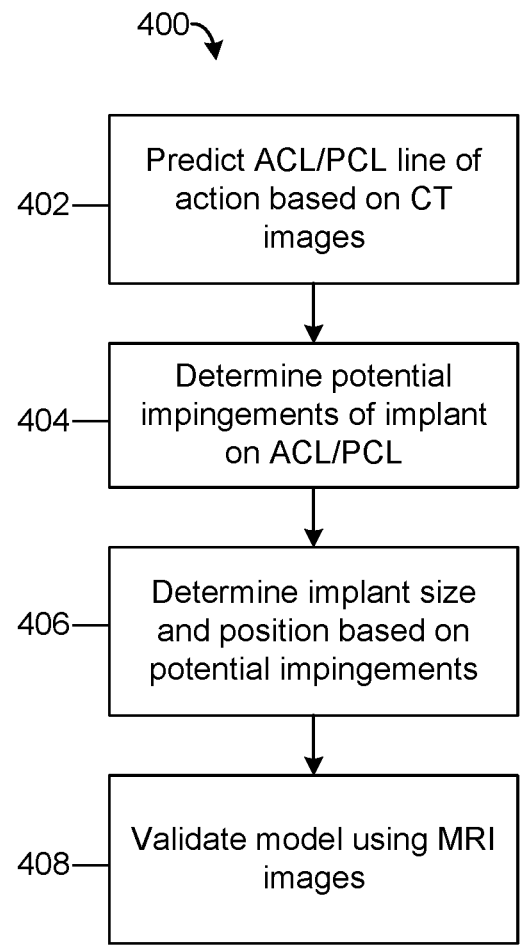
FIG. 4 is a flowchart of a process for preventing impingement in a knee arthroscopy procedure, according to an exemplary embodiment.

Referring now to FIG. 4, a process 400 for preventing impingement of a patient's ACL and/or PCL by implant components is shown, according to an exemplary embodiment. The process 400 may be carried out by the surgical system 100 of FIG. 1 with the processing circuit 160 shown in FIG. 2. Although described herein in an application for total knee arthroplasty, process 400 may also be used for partial knee arthroplasty, early intervention knee surgeries, etc. Process 400 may be particularly well suited for bicruciate-retaining knee arthroplasty procedures. Process 400 may be an example of step 310 of process 300 shown in FIG. 3.

At step 402, the processing circuit 160 predicts the ACL/PCL line of action based on CT images. Based on the CT images, the virtual bone model, and/or identified ACL and PCL attachment points on the femur 106 and tibia 108, the processing circuit 160 predicts the space through which the ACL and PCL extend through a full range of motion of the knee. For example, the processing circuit 160 may generate a model of the ACL and/or PCL to add to the virtual bone model.

At step 404, the processing circuit 160 determines potential impingements of the ACL or PCL by the implant. The processing circuit 160 may generate virtual implant models and overlay the virtual implant models on the virtual bone model as described above with reference to FIG. 3. The ACL/PCL model may also be included. The processing circuit 160 may thereby obtain a virtual model that includes a virtual bone model, virtual implant model, and virtual ligament model. The processing circuit 160 may test the virtual model through a full range of motion and detect any overlap between the virtual implant model and the virtual ligament model indicative of potential impingements. Overlap between the virtual implant model and the virtual ligament model indicates that impingement is likely if the implant is installed as represented in the model.

At step 406, the processing circuit 160 chooses the implant size and position based on potential impingements. That is, the processing circuit 160 chooses the implant size and position to eliminate potential impingements or minimize the risk of impingement. For example, the processing circuit 160 may alter the implant size and position such that the virtual model may be tested through a full range of motion without creating any overlap between the virtual implant model and the virtual ligament model. The processing circuit 160 may use imaging, as described above with respect to FIG. 5, to determine the proper size and position of the implant to avoid impingement. In embodiments where a graphical user interface is provided that allows a user to alter the planned implant size and position, the processing circuit 160 may generate a warning or alert that indicates to a user that a proposed planned implant position is predicted to cause impingement. The processing circuit 160 may also prevent the user from selecting an option in which an impingement is predicted or for which the risk of impingement exceeds a threshold.

At step 408, the processing circuit 160 validates the virtual model and the impingement predictions using MRI images. The processing circuit 160 may receive MRI images from a preoperative imaging system 218. The MRI images may be segmented to distinguish the femur, tibia, patella, cartilage, and ligaments (e.g., ACL, PCL, patellar ligament) in the knee. One or more three-dimensional models of the bones, ligaments, and cartilage may be generated, for example using a similar approach as described for CT images above. Virtual models of the planned implants may be positioned in the MRI-based three-dimensional models. These models may then be used to validate that the CT-based models correctly predicted impingement or non-impingement. For example, if the MM-based model predicts non-impingement and the CT-based model predicts non-impingement, then the MM-based model validates the CT-based model and the planned position of the implant may be approved. The process may continue with the generation of patient-specific control objects based on the implant size and position selected to prevent potential soft tissue impingements, as described above with respect to steps 312 and 314 of process 300.

Referring now to FIGS. 6-9, various views of a graphical user interface 500 generated by the processing circuit 160 (e.g., by the user interface circuit 204) and displayed by the input/output device 162 (i.e., shown on display 164) are shown, according to exemplary embodiments. In each of FIGS. 6-9, the graphical user interface 500 includes an upper row 502 showing visualizations of a virtual bone model of the femur 106 (virtual femur model 550) and a lower row 504 showing visualizations of a virtual bone model of the tibia 108 (virtual tibia model 552). The graphical user interface 500 also includes three columns corresponding to three pairs of visualizations of the virtual femur model 550 and the virtual tibia model 552. The first column 506 shows front views of the virtual femur model 550 and virtual tibia model 552, the second column 508 shows distal views of the virtual femur model 550 and virtual tibia model 552, and the third column 510 shows side views of the virtual femur model 550 and virtual tibia model 552. In addition, FIGS. 6, 7, 8A, and 9 include visualizations of a virtual femoral implant 554 and visualizations of a virtual tibial implant 556. The graphical user interface 500 thereby displays a planned implant placement to a user.

In the configuration shown in FIG. 6, the graphical user interface 500 shows cross-sectional views of the virtual femur model 550, the virtual femoral implant 554, the virtual tibia model 552, and the virtual tibial implant 556. A circle 558 encircles (e.g., is centered on) the PCL attachment point on the virtual tibia model 552. In some embodiments, the position of the circle 558 is adjustable by a user to alter the definition of the position of the PCL attachment point. A dashed line 560 indicates a height or plane associated with the PCL attachment point. In some embodiments, the dashed line 560 is adjustable by a user to move the position of the PCL attachment point. As shown in FIG. 6, the virtual tibial implant 556 is positioned to not interfere with the PCL attachment point.

In the configuration shown in FIG. 6, the graphical user interface 500 shows three-dimensional renderings of the virtual femur model 550, the virtual femoral implant 554, the virtual tibia model 552, and the virtual tibial implant 556. The virtual femur model 550 and the virtual tibia model 552 are modified to show the effects of the planned cuts to femur 106 and tibia 108. That is, portions of the femur 106 and tibia 108 to be removed during surgery have also been removed from the virtual femur model 550 and the virtual tibia model 552. A user may then check whether the planned cuts will alter, damage, intersect, interfere, or otherwise affect one or more soft tissue attachment points. The graphical user interface 500 includes arrow buttons 600 that allow a user to adjust the position, size, rotation, etc. of the virtual femoral implant 554 and the virtual tibial implant 556.

Figure 8A:
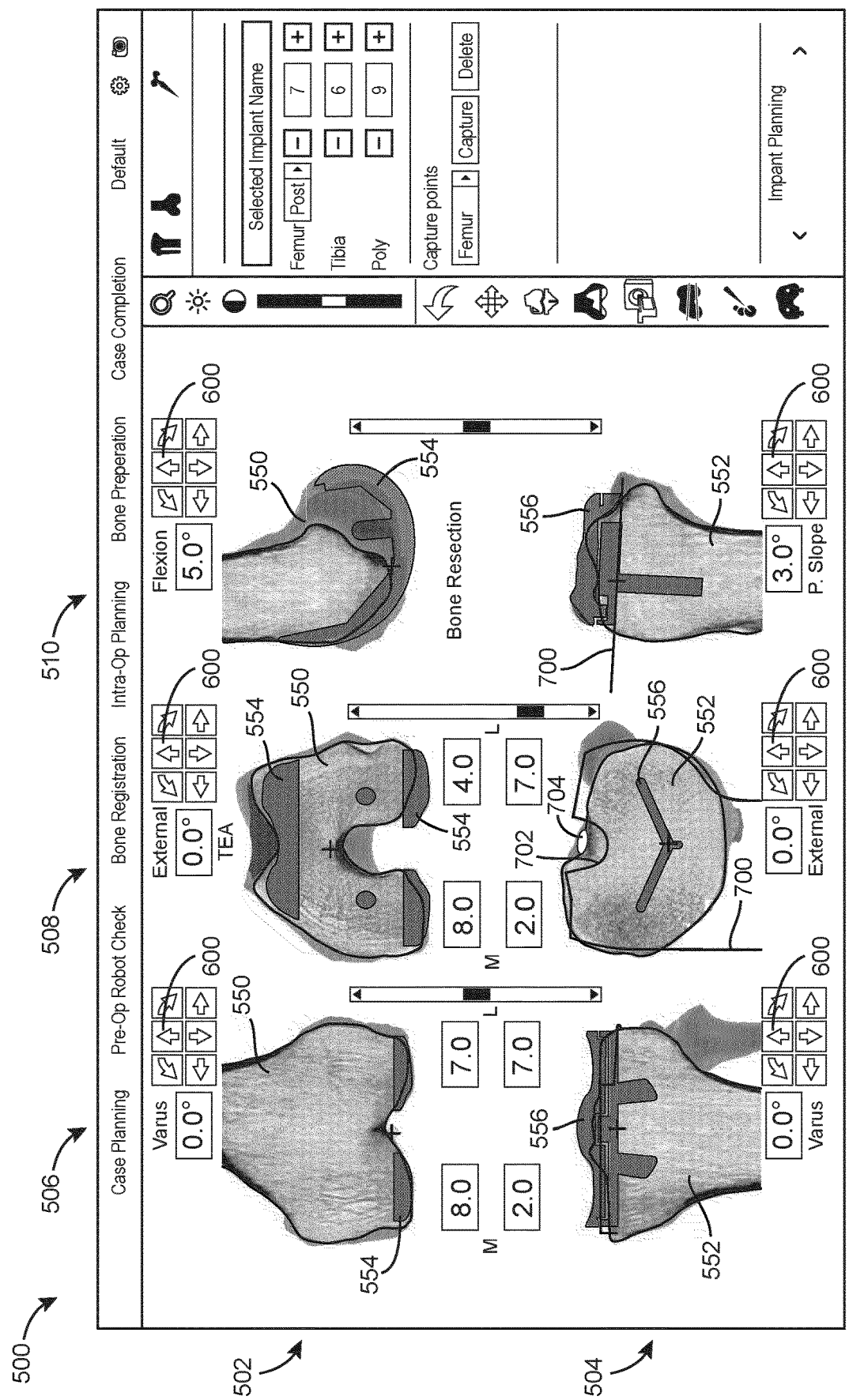
FIG. 8A is a third illustration of a graphical user interface generated by the processing circuit of FIG. 2, according to an exemplary embodiment.

In the configuration shown in FIG. 8A, the graphical user interface 500 shows cross-sectional views of the virtual femur model 550, the virtual femoral implant 554, the virtual tibia model 552, and the virtual tibial implant 556. In FIG. 8A, a virtual boundary 700 illustrates a boundary of a control object. The virtual boundary 700 defines a boundary that the surgical tool 134 is confined from crossing by the control object and the robotic device 120. As shown in FIG. 8, the virtual boundary 700 includes a concave notch 702 where the virtual boundary 700 curves around the PCL attachment point indicated by highlighting 704. The virtual boundary 700 thereby indicates that the control object is configured to confine the surgical tool 134 from reaching the PCL attachment point.

Figure 8B:
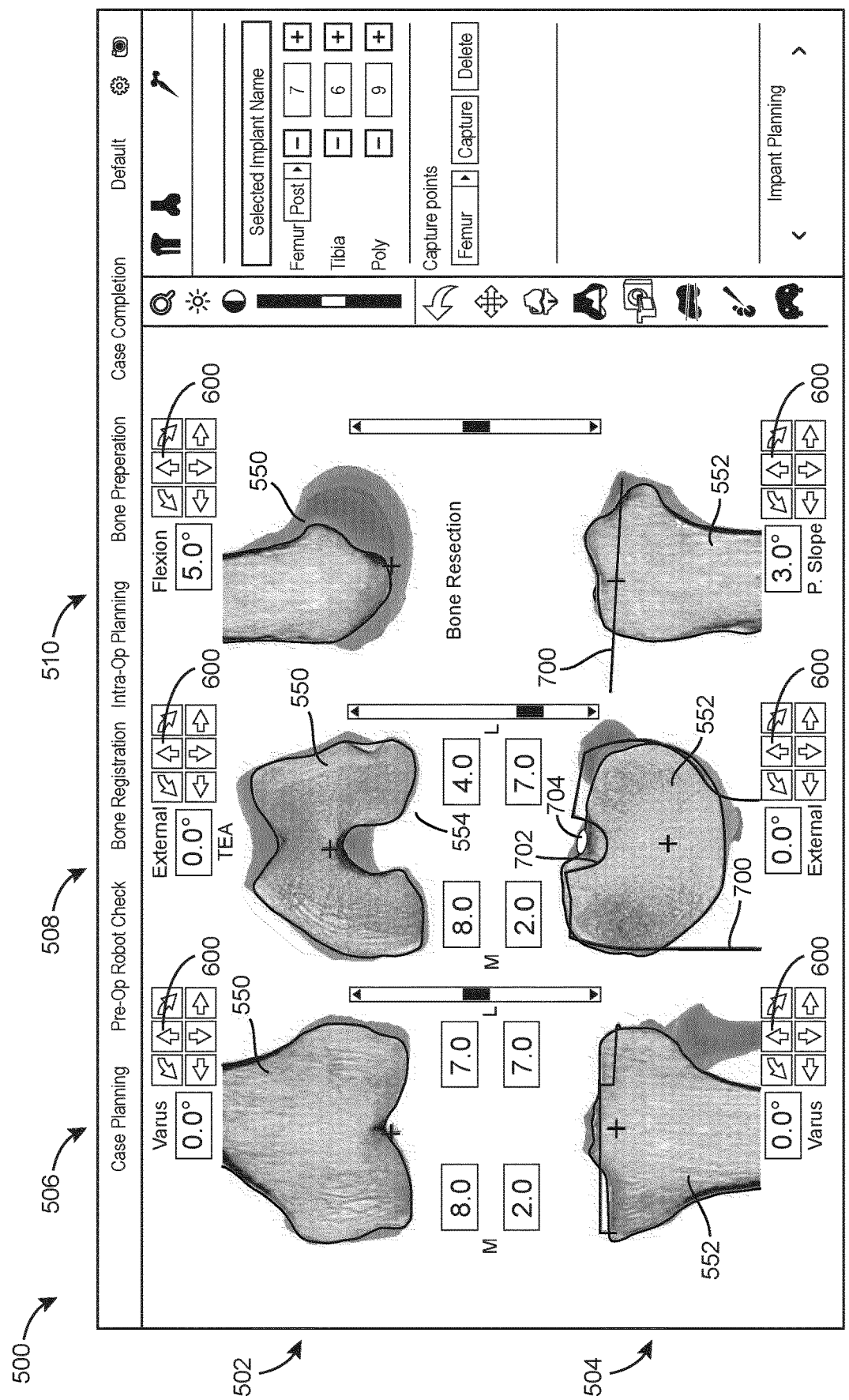
FIG. 8B is a fourth illustration of a graphical user interface generated by the processing circuit of FIG. 2, according to an exemplary embodiment.
Figure 8C:
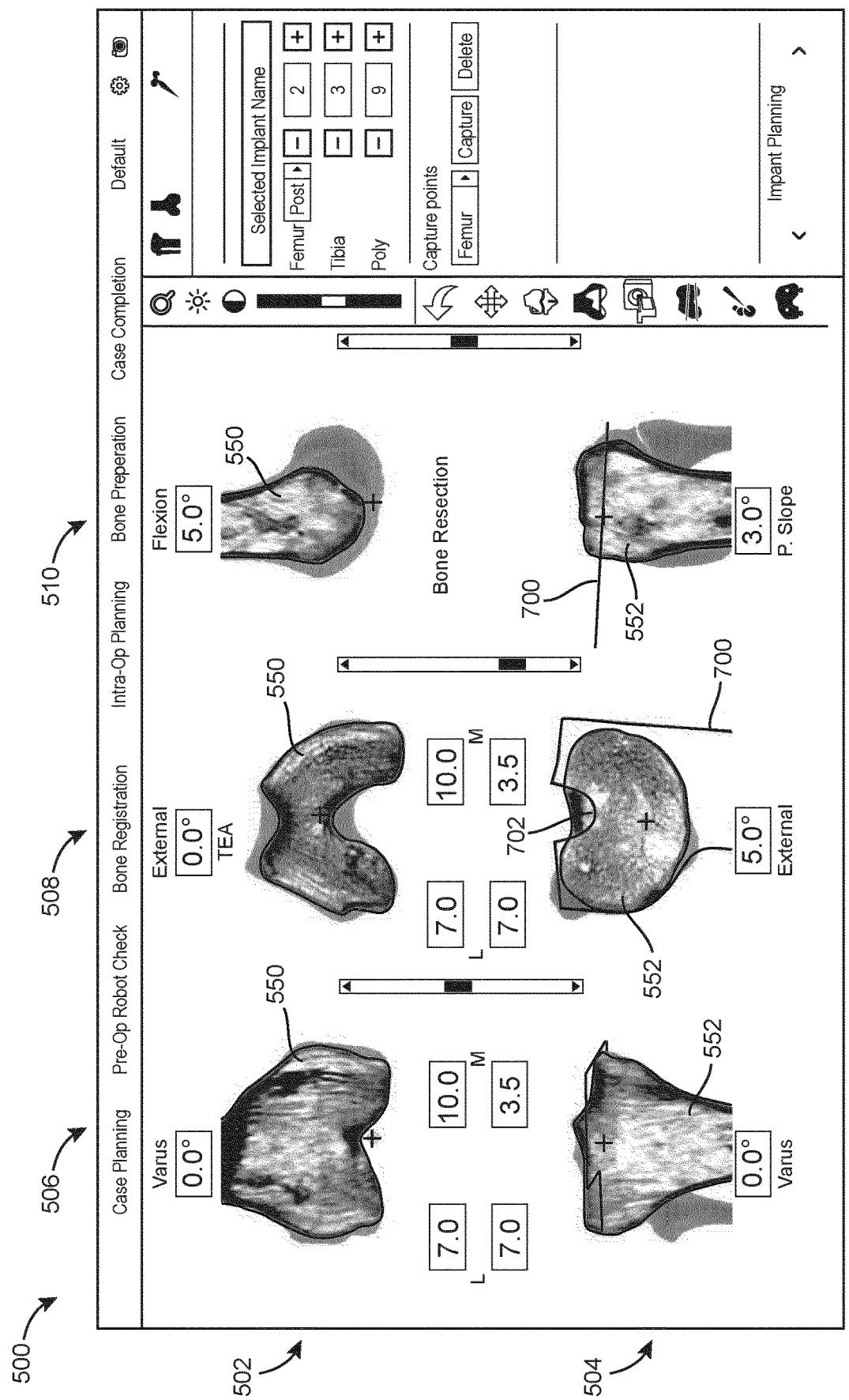
FIG. 8C is a fifth illustration of a graphical user interface generated by the processing circuit of FIG. 2, according to an exemplary embodiment.
Figure 9:
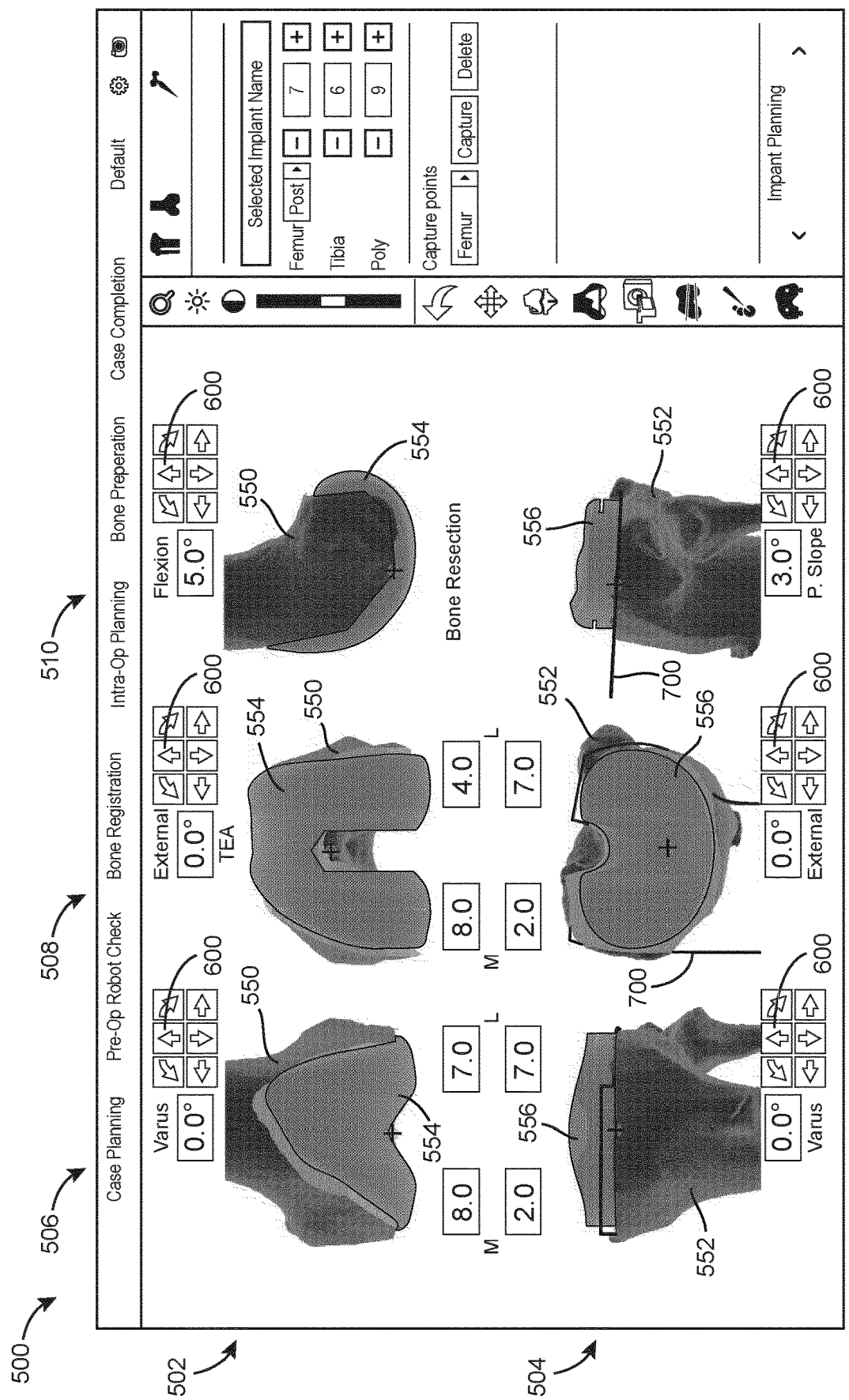
FIG. 9 is an eighth illustration of a graphical user interface generated by the processing circuit of FIG. 2, according to an exemplary embodiment.

In the configuration shown in FIGS. 8B-C, the graphical user interface 500 shows cross-sectional views of the virtual femur model 550 and the virtual tibia model 552 with the virtual boundary 700 corresponding to a planned tibial cut. FIG. 8B shows a view for right knee while FIG. 8C shows a view for a left knee. As shown in FIGS. 8B-C, the virtual femur model 550 and the virtual tibia model 552 may be visualized to include CT images and/or other medical images that show the bone density in various areas of the patient's femur and tibia. This may be useful for a user in identifying one or more soft tissue attachment points, identifying strong areas of bone suitable for engagement with an implant, and/or for other planning or diagnostic purposes. As shown in FIGS. 8B-C, the virtual femoral implant 554 and the virtual tibial implant 556 are hidden from the graphical user interface 500, presenting a simplified view that allows a user to clearly view a planned cut facilitated by the virtual boundary 700.

Figure 8D:
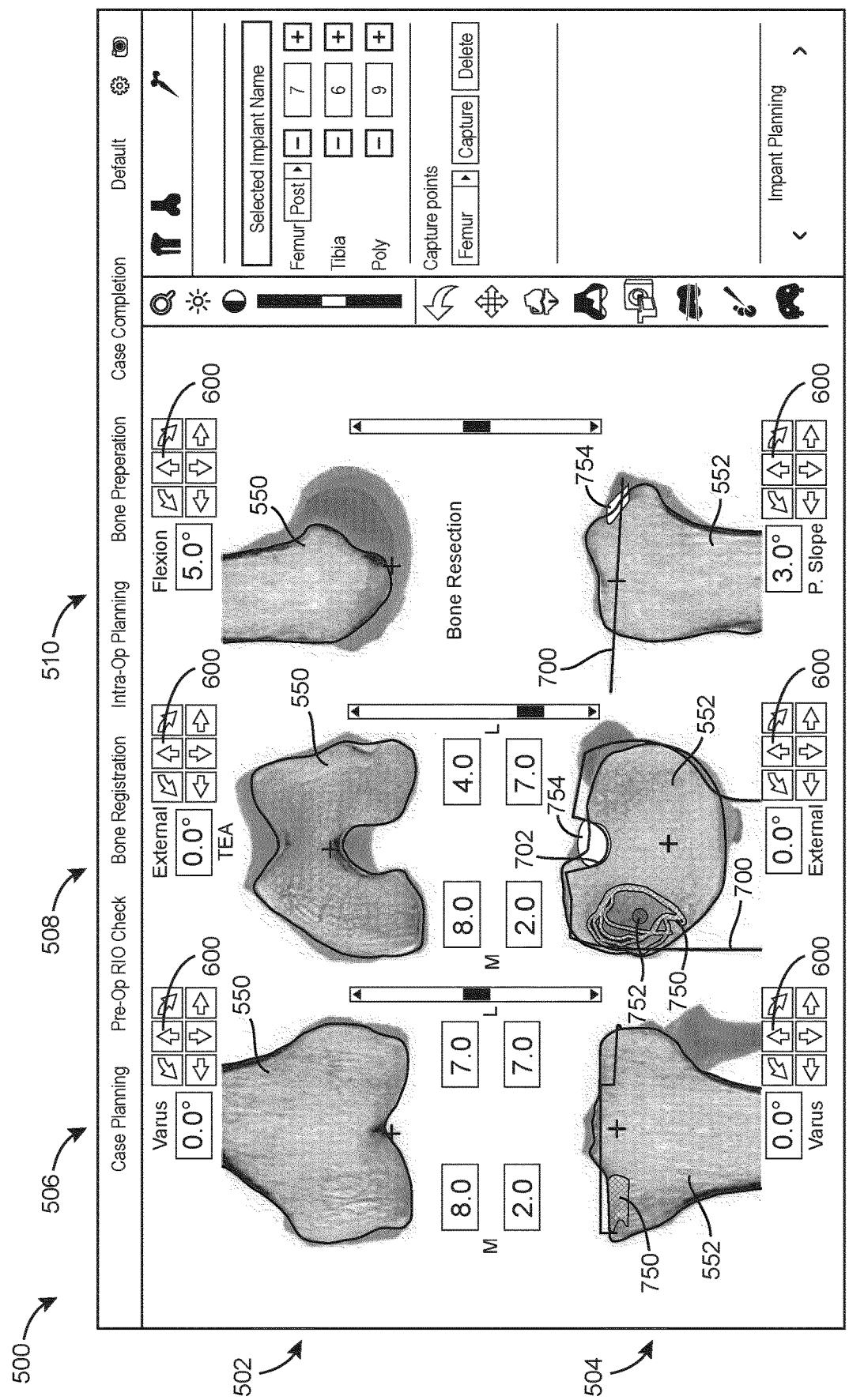
FIG. 8D is a sixth illustration of a graphical user interface generated by the processing circuit of FIG. 2, according to an exemplary embodiment.
Figure 8E:
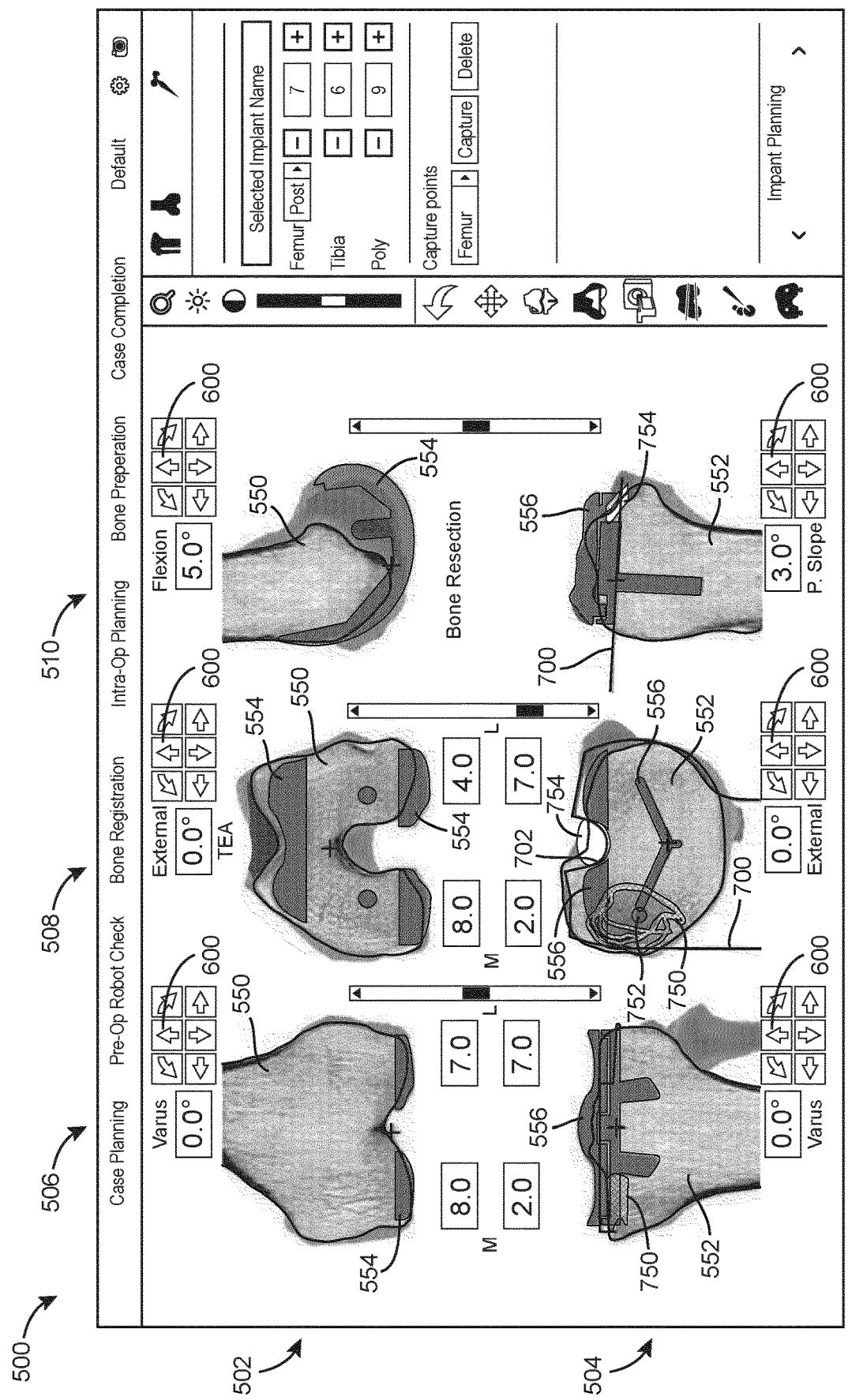
FIG. 8E is a seventh illustration of a graphical user interface generated by the processing circuit of FIG. 2, according to an exemplary embodiment.

As shown in FIGS. 8D-E, bone regions having a higher density may be shown as color-coded regions, shaded regions, or regions indicated by other demarcation on the graphical user interface 500. In the example shown, demarcation 750 indicates a bone dense region. Point 752 indicates the centroid of the bone dense region. Region 754 corresponds to the PCL and/or the PCL attachment point. The demarcation 750, the point 752, and/or the region 754 may facilitate implant planning. For example, a surgeon (user) could align the sulcus of the virtual tibial implant 556 to the point 752 (as shown in FIG. 8E) to optimize internal/external rotation. As another example, a surgeon could align the varus/valgus rotation of the tibial resection to optimize the density of the cut plane. Various further alignments and planning advantageous may be facilitated by including the demarcation 750, the point 752, and/or the region 754 on the graphical user interface 500.

In the configuration shown in FIG. 9, the graphical user interface 500 shows three-dimensional renderings of the virtual femur model 550, the virtual femoral implant 554, the virtual tibia model 552, and the virtual tibial implant 556. FIG. 9 also shows the virtual boundary 700. In the embodiment shown, the control object is planar control object, oriented such that virtual boundary 700 is only viewable from the distal view of the second column 508. The graphical user interface 500 includes arrow buttons 600 that allow a user to adjust the position, size, rotation, etc. of the virtual femoral implant 554 and the virtual tibial implant 556. In response to a user input to adjust the position, size, rotation, etc. of the virtual tibial implant 556, the processing circuit 160 adjusts the control object accordingly. The virtual boundary 700 on the graphical user interface 500 is updated as well. Thus, the user may adjust the virtual boundary 700 as desired by adjusting the position, size, rotation, etc. of the virtual tibial implant 556.

Figure 10:
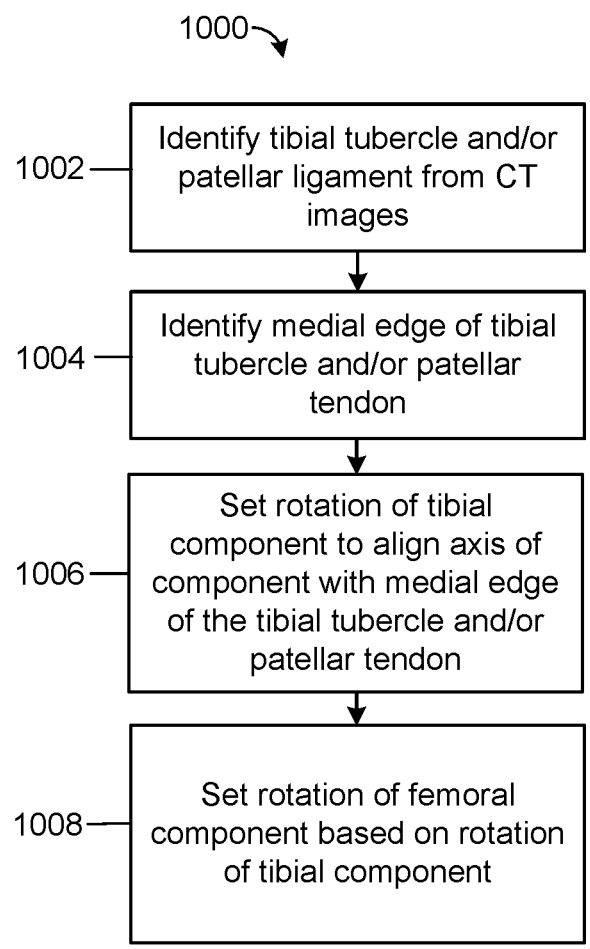
FIG. 10 is a flowchart of a process for determining a rotational alignment of an implant component, according to an exemplary embodiment.
Figure 11:
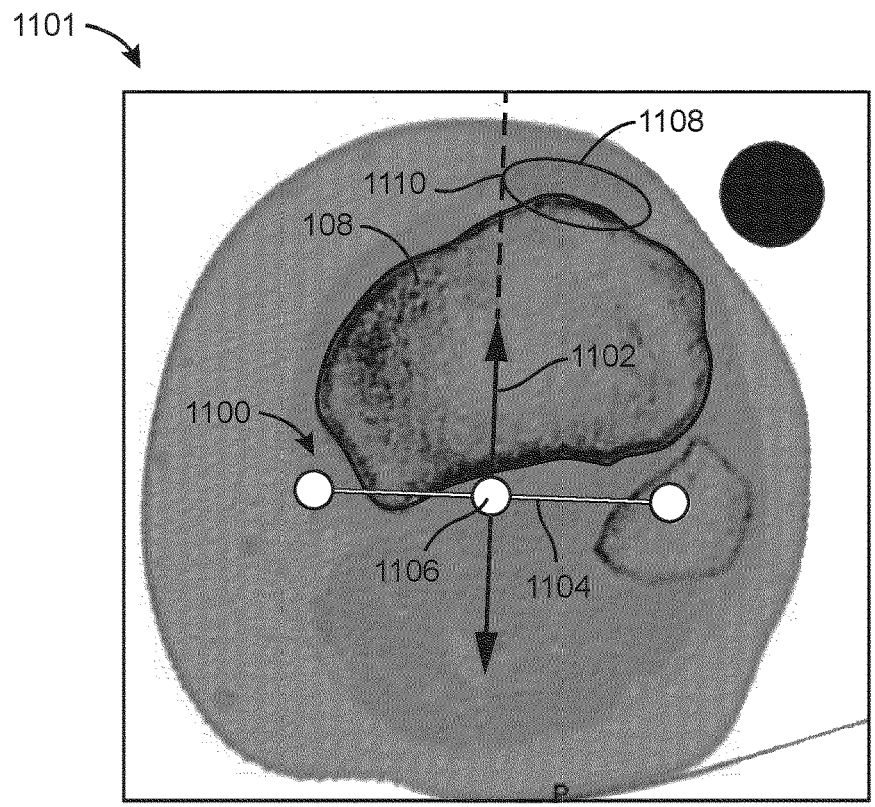
FIG. 11 is an illustration of a part of the process of FIG. 10, according to an exemplary embodiment.
Figure 12:
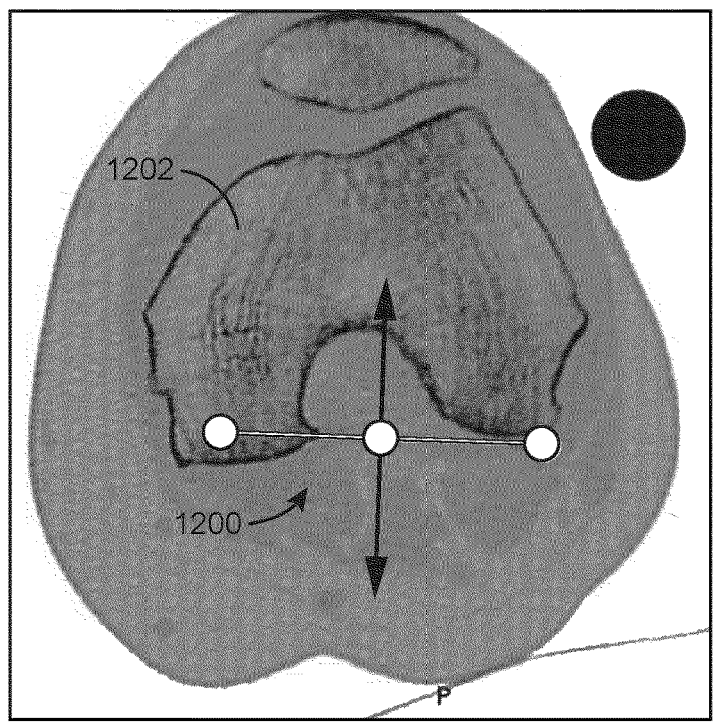
FIG. 12 is an illustration of a part of the process of FIG. 10, according to an exemplary embodiment.

Referring now to FIGS. 10-12, a process 1000 for determining a rotational alignment of an implant based on the attachment of the patellar ligament to the tibia is illustrated, according to an exemplary embodiment. FIG. 10 shows a flowchart of process 1000. FIGS. 11-12 show illustrations useful in explanation of process 1000. Process 1000 can be carried out by the processing circuit 160 of FIG. 1. Process 1000 may be included as part of an embodiment of process 300 of FIG. 3, for example with steps 304-310 of FIG. 3.

At step 1002, the tibial and the patellar ligament are identified from CT images to identify a patellar ligament attachment point (tibial tubercle). That is, the CT images are segmented to define pixels or coordinates on the CT images corresponding to the tibial tubercle and/or the patellar ligament. Segmenting the image to identify the patellar ligament and the tibia facilitates identification of a region where the patellar ligament attaches to the tibia (e.g., where the segmented areas abut one another). In some embodiments, the processing circuit 160 automatically identifies the tibial tubercle and/or the patellar ligament in the CT images (i.e., auto-segmentation). In other embodiments, the processing circuit 160 generates a graphical user interface that prompts a user to input an indication of a location (e.g., outline, area) of the patellar ligament and/or the tibial tubercle. The processing circuit 160 may receive the user input and identify the location of the tibial tubercle and/or the patellar ligament based on the user input. For example, FIG. 10 shows a segmentation border 1008 identified as the outside border of the patellar ligament at the tibial tubercle.

At step 1004, the medial edge of the patellar ligament at the tibial tubercle is identified. In other words, the processing circuit 160 determines the furthest-medial point of the patellar ligament at the tibial tubercle where the patellar ligament attaches to the tibia (i.e., medial extremum point 1110 in FIG. 11). To identify this point, a CT image 'slice' at the level of the tibial tubercle is chosen that shows attachment between the patellar ligament and the tibia (e.g., CT image 1101 of FIG. 11). At that level, the furthest medial point of the tibial tubercle and/or the patellar ligament is determined based on segmentation data from step 1002, for example by selecting, from the segmented region corresponding to the patellar ligament, the point closest to the medial border of the CT image. The processing circuit 160 thereby determines coordinates associated with the medial edge of the tibial tubercle and/or patellar ligament.

At step 1006, the rotation of a tibial component of a prosthetic implant is determined by aligning an axis of the tibial component with the medial edge of the tibial tubercle and/or patellar ligament (i.e., with the medial extremum of the attachment region of the patellar ligament on the tibia). The processing circuit 160 generates a virtual implant model of the tibial component (e.g., virtual tibial implant 556) to align relative to a virtual bone model (e.g., as generated at step 306 of process 300). In some visualizations of the virtual implant model, for example as shown in FIG. 11, the virtual implant model may include a representation 1100 of two or more axes that define one or more rotations of the virtual implant model. More particularly, representation 1100 illustrates the rotational alignment of the virtual tibial implant overlaid on a CT image 1001 of the tibia 108.

As shown in FIG. 11, a first axis 1102 of representation 1100 may extend substantially side-to-side (i.e., medial to lateral) while a second axis 1004 may point perpendicular to the first axis 1102 in the plane of the CT image (i.e., a plane defined by a normal vector substantially parallel with a length of the tibia). The rotational alignment of the virtual implant model may be adjusted by rotating the first axis 1102 and the second axis 1104 about an intersection point 1106 of the first axis 1102 and the second axis 1104 in the plane of the CT image.

In step 1006, the processing circuit 160 defines the rotation of the virtual tibia model such that the second axis 1104 intersects the medial edge of the patellar ligament at the attachment point/region between the patellar ligament and the tibia. As shown in FIG. 11, the second axis 1104 extends through the medial extremum point 1110 of a segmentation border 1108 corresponding to the patellar ligament. In other words, the rotation of the virtual tibial implant is set to ensure that the second axis 1104 shown in FIG. 11 passes through the medial extremum coordinates identified at step 1004.

At step 1008, the rotational alignment of the virtual tibial implant is used to determine the rotational alignment of a virtual model of the femoral component of an implant (e.g., virtual femoral implant 554). For example, the rotational alignment of the virtual tibial implant and the rotational alignment of the virtual femoral implant may have a preset geometric relationship that may be used by the processing circuit 160 to determine the rotational alignment of the virtual femoral implant based on the rotational alignment of the virtual tibial implant. FIG. 12 shows a representation 1200 of the alignment of the virtual femoral implant on the femur (i.e., overlaid on a CT image 1202 of the femur). As shown in FIG. 12, the representation 1200 of the alignment of the virtual femoral implant matches the representation 1100 of the alignment of the virtual tibial implant.

The processing circuit 160 thereby determines the rotational alignment of the implant based on the attachment point of the patellar ligament to the tibia.

As mentioned above, process 1000 may be implemented as a sub-part of process 300. Accordingly, after step 1008 the process circuit 160 may determine other sizing or placement characteristics of the implant (i.e., at step 310), generate a control object based on the determined implant placement and the attachment point of the patellar ligament to the tibia (i.e., at step 312), and constrain or control the surgical tool 134 based on the control object (i.e., at step 314).

In some embodiments, process 1000 further includes a step of using sulcus density in determining tibial baseplate orientation in the axial, coronal, and sagittal planes to achieve neutral implant alignment. In some embodiments, coronal and sagittal density profiles may be used to determine good bone stock for optimal implant fixation.

Referring now to FIG. 13, a graphical user interface 1300 is shown, according to an exemplary embodiment. The graphical user interface 1300 may be generated by the processing circuit 160 (e.g., by the user interface circuit 204) and displayed by the input/output device 162 (i.e., shown on display 164). In some embodiments, the graphical user interface 1300 corresponds to a portion of graphical user interface 500, for example the portion found at the second column 508 and the lower row 504 in FIG. 7.

In the embodiment of FIG. 13, a tool visualization 1302 of the surgical tool 134 is overlaid on a cross-sectional end view of the virtual tibia model 552 (e.g., on a tibia shown by a CT image). The position of the tool visualization 1302 may be updated in real-time to show the real position of the surgical tool 134 relative to the real tibia 108, for example based on tracking/navigation data generated by the tracking system 122. The graphical user interface 1300 also includes the virtual boundary 700 and an indicator 1304 that highlights the location of the PCL attachment point. A user (e.g., a surgeon) may thereby view the relative position of the surgical tool 134, the virtual boundary 700, and the attachment point indicated by indicator 1304 on the graphical user interface 1300 during the surgical operation. The user may thereby be assisted in properly positioning and/or orienting a cut made using the surgical tool 134 relative to the attachment point.

While the present disclosure is focused on the PCL and ACL, the systems and methods described herein may be adapted for identifying and protecting other soft tissue such as the medial collateral ligament (MCL). Various such possibilities are contemplated by the present disclosure.

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A surgical system, comprising:
a robotic device;
a surgical tool mounted on the robotic device; and
a processing circuit configured to:
plan placement of an implant by aligning an axis of the implant with a medial edge of a soft tissue attachment point of a virtual bone model;
generate a control object based on the placement of the implant; and
control the robotic device in accordance with the control object.

2. The surgical system of claim 1, wherein the soft tissue attachment point corresponds to a site where a posterior cruciate ligament or an anterior cruciate ligament attaches to a femur or a tibia.

3. The surgical system of claim 1, wherein the soft tissue attachment point corresponds to a site where a patellar ligament attaches to a tibia.

4. The surgical system of claim 1, the processing circuit further configured to generate a graphical user interface, the graphical user interface comprising a visualization of the virtual bone model, the implant, and the soft tissue attachment point.

5. The surgical system of claim 4, the graphical user interface further comprising a visualization of the control object.

6. The surgical system of claim 1, wherein the processing circuit is further configured to restrict the control object from containing the soft tissue attachment point.

7. A method, comprising:
identifying a medial edge of a soft tissue attachment point of a virtual bone model;
planning implant placement by aligning an axis of an implant with the medial edge of the soft tissue attachment point;
generating a control object based on the implant placement; and
constraining or controlling a surgical tool mounted on a robotic device based on the control object.

8. The method of claim 7, further comprising generating the virtual bone model based on image data, wherein the image data comprises computed tomography images, and wherein the method further comprises segmenting the computed tomography images to identify one or more bones in the images.

9. The method of claim 7, wherein the soft tissue attachment point corresponds to a site where a posterior cruciate ligament or an anterior cruciate ligament attaches to a femur or a tibia.

10. The method of claim 7, wherein the soft tissue attachment point corresponds to a site where a patellar ligament attaches to a tibia.

11. The method of claim 7, further comprising generating a graphical user interface that visualizes the virtual bone model, the implant, and the soft tissue attachment point.

12. The method of claim 11, wherein the graphical user interface further provides a visualization of the control object.

13. The method of claim 7, further comprising:
predicting a line of action of a ligament based on the soft tissue attachment point;
augmenting the virtual bone model with a virtual implant model of the implant;
determining whether the line of action of the ligament intersects the virtual implant model; and
in response to a determination that the line of action of the ligament intersects the virtual implant model, providing an alert to a user.

14. The method of claim 7, further comprising restricting the control object from containing the soft tissue attachment point.

15. Non-transitory computer-readable media storing program instructions that, when executed by one or more processors, cause the one or more processors to perform operations comprising:
identifying a soft tissue attachment point of a virtual bone model;
planning implant placement by aligning an axis of an implant with a medial edge of the soft tissue attachment point;
generating a control object based on the implant placement; and
constraining or controlling a surgical tool mounted on a robotic device based on the control object.

16. The computer-readable media of claim 15, wherein the operations comprise restricting the control object from containing the soft tissue attachment point.

17. The computer-readable media of claim 15, the operations comprising predicting a line of action of a ligament based on the soft tissue attachment point;
augmenting the virtual bone model with a virtual implant model of the implant;
determining whether the line of action of the ligament intersects the virtual implant model; and
in response to a determination that the line of action of the ligament intersects the virtual implant model, providing an alert to a user.

* * * * *